United States Patent
Maslyn et al.

(10) Patent No.: US 6,408,308 B1
(45) Date of Patent: Jun. 18, 2002

(54) SYSTEM AND METHOD FOR GENERATING, ANALYZING AND STORING NORMALIZED EXPRESSION DATASETS FROM RAW EXPRESSION DATASETS DERIVED FROM MICROARRAY INCLUDES NUCLEIC ACID PROBE SEQUENCES

(75) Inventors: Timothy J. Maslyn, Cupertino; Srikar D. Rao, Santa Clara; Benjamin G. Cocks, Palo Alto; Rachel J. Cheng, Los Altos; Timothy M. Engler, Palo Alto; James R. Kerr, Redwood City; Steven M. Lassagne, Palo Alto; Jeffrey J. Seilhamer, Los Altos Hills, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/106,607

(22) Filed: Jun. 29, 1998

Related U.S. Application Data

(60) Provisional application No. 60/073,045, filed on Jan. 29, 1998, and provisional application No. 60/079,094, filed on Mar. 23, 1998.

(51) Int. Cl.[7] .............................................. G06F 17/30

(52) U.S. Cl. ........................ 707/104.1; 702/19; 702/20; 435/6; 435/287.2; 536/24.5

(58) Field of Search ............................... 702/19–21, 27; 707/1–6, 100–104; 435/3–6, 303, 71.1–71.3, 287.2; 436/278–279; 706/924; 703/11–12; 382/128–129; 536/24.5

(56) References Cited

U.S. PATENT DOCUMENTS

| | | | | |
|---|---|---|---|---|
| 5,418,944 A | * | 5/1995 | DiPace et al. | 707/1 |
| 5,726,018 A | * | 3/1998 | Pasternack | 435/6 |
| 5,752,019 A | * | 5/1998 | Rigoutsos et al. | 707/3 |
| 5,778,375 A | * | 7/1998 | Hecht | 707/101 |
| 5,974,164 A | * | 10/1999 | Chee | 382/129 |
| 6,023,659 A | * | 2/2000 | Seilhamer et al. | 702/19 |

FOREIGN PATENT DOCUMENTS

| | | | | |
|---|---|---|---|---|
| EP | 0646883 A1 | * | 4/1995 | G06F/1/30 |

OTHER PUBLICATIONS

Apweiler R et al., Introduction to Database Modeling in Bioinformatics, EMBL Outstation, European Bioinformatics Institute, Hinxton, Cambridge, UK, and 1–19, 1999.*

Leming Shi, DNA Microarray (Genomie Chip), www.Gene–Chip.com, 1–17, 1998.*

Wang Chiew Tan et al., QUICK:graphical user interface to multiple databases, Database and Expert system applications, proceedings, seventh international workshop, 404–409, Sep. 1996.*

(List continued on next page.)

*Primary Examiner*—John Breene
*Assistant Examiner*—Srirama Channavajjala
(74) *Attorney, Agent, or Firm*—Squire, Sanders, Dempsey LLP

(57) ABSTRACT

A biomolecular expression information processing system has procedures and tables that store abundance datasets and hybridization data. The tables also store information identifying a microarray technology type for each hybridization and microarray design information for each microarray technology type. The microarray design information includes technology data that specifies global characteristics of each microarray, and array element data that specifies characteristics of array elements in each microarray instance of the microarray technology type. The procedures process the abundance datasets in accordance with the microarray design information associated with each such abundance dataset. The system stores technology data for multiple distinct microarray technology types and stores array element data for multiple microarray designs of a single technology type.

50 Claims, 28 Drawing Sheets

OTHER PUBLICATIONS

Imai, T et al., Implementing an Integrated system for heterogeneous molecular biology databases with intelligent agents, IEEE communications, computers and signal processing 10 years PACRIM 1987–1997–Networking the pacific Rim 1997 conference, vol 2, 807–810, Aug. 1997.*

GCG Transcript, bio–computing news for users of GCG products, vol. 8, No. 2, fall 2000, www.gcg.com/pub/newsletter/vol8_no2_fall2000.html, 2000.*

* cited by examiner

90 PMDDataSource Table

| PMD Data Source | primary key | Char(10) |
|---|---|---|
| PMD Data Source Description | | Char(40) |

*FIG. 7A*

_98_ Donor Tables
TissueSpeciman Table

| Donor ID | primary key | int |
|---|---|---|
| PMD Data Source | primary key | Char(10) |
| TissueID | primary key | int |
| Tissue Type | | Char(40) |
| Organ | | Char(40) |
| Gross Description | | Char(80) |

DonorSnapshot Table

| Donor ID | primary key | int |
|---|---|---|
| PMD Data Source | primary key | Char(10) |
| Species | | Char(40) |
| DevelopStage | | Char(15) |
| Age | | int |
| Weight | | int |
| Cause of death | | Char(40) |

DonorTissue Table

| Donor ID | primary key | int |
|---|---|---|
| PMD Data Source | primary key | Char(10) |
| Tissue ID | primary key | int |

FIG. 7B

_94_ Microarray Design Tables

Technology Table

| Technology Type | primary key | Char(10) |
|---|---|---|
| Technology Description | | Char(40) |
| Display Shape | | Char(1) |

Design Table

| Array Design ID | primary key | Char(10) |
|---|---|---|
| Technology Type | primary key, foreign key | Char(10) |
| PMD Data Source | primary key, foreign key | Char(10) |
| Array Design Name | | Char(25) |
| NumArrayElements | | int |
| Comments | | Char(255) |

SummaryArrayElement Table

| Array Design ID | primary key, foreign key | Char(10) |
|---|---|---|
| Technology Type | primary key, foreign key | Char(10) |
| PMD Data Source | primary key, foreign key | Char(10) |
| SummaryElementID | primary key | int |
| TranscriptID | foreign key | Char(15) |
| Control Transcript Y/N | | Char(1) |
| Summary Row | | int |
| Summary Column | | int |
| Concentration | | float |
| Unit | | Char(10) |

*FIG. 7C*

_96_ Hybridization Tables

Hybridization Table

| Hyb_ID | primary key | Char(10) |
|---|---|---|
| PMD_Data_Source | primary key, foreign key | Char(10) |
| Hyb_Name | | Char(25) |
| Array_Design_ID | foreign key | Char(10) |
| TechnologyType | foreign key | Char(10) |
| ArrayPMDDataSource | foreign key | Char(10) |
| ArrayExperimentID | foreign key | Char(10) |
| Duration | | int |
| TimeUnit | | Char(2) |
| RunDate | | Date |

ArrayExperiment Table

| ArrayExperimentID | primary key | Char(10) |
|---|---|---|
| PMDDataSource | primary key, foreign key | Char(10) |
| ExperimentDescription | | Char(40) |

HybPrepSample Table

| HybID | primary key, foreign key | Char(10) |
|---|---|---|
| PMDDataSource | primary key, foreign key | Char(10) |
| PrepSampleID | primary key, foreign key | Char(10) |
| ControlSample_YN | | Char(1) |

FIG. 7D

Image Table

| HybID | primary key, foreign key | Char(10) |
|---|---|---|
| PMDDataSource | primary key, foreign key | Char(10) |
| ImageID | primary key | Char(10) |
| PrepSampleID | foreign key | Char(10) |
| ImageDescription | | Char(80) |
| CombinedYN | | Char(1) |

ImageDetail Table

| HybID | primary key, foreign key | Char(10) |
|---|---|---|
| PMDDataSource | primary key, foreign key | Char(10) |
| ImageID | primary key | Char(10) |
| ImageDetailID | primary key | Number(8) |
| ArrayDesignID | foreign key | Char(10) |
| TechnologyType | foreign key | Char(10) |
| ArrayPMDDataSource | foreign key | Char(10) |
| SummaryElementID | foreign key | int |
| Intensity | | Float |
| FluorescenceError | | Float |

FIG. 7E

Summarized Intensity Table

| HybID | primary key, foreign key | Char(10) |
|---|---|---|
| PMDDataSource | primary key, foreign key | Char(10) |
| ImageID | primary key, foreign key | Char(10) |
| SummaryElementID | primary key, foreign key | int |
| IntSummMethodID | primary key, foreign key | Char(10) |
| ArrayDesignID | foreign key | Char(10) |
| TechnologyType | foreign key | Char(10) |
| ArrayPMDDataSource | foreign key | Char(10) |
| SummarizedIntensity | | Float |
| SummarizationError | | Float |

IntensitySummMethod Table

| IntSummMethodID | primary key | Char(10) |
|---|---|---|
| IntSummMethodDescription | | Char(80) |

SummarizedImage Table

| HybID | primary key, foreign key | Char(10) |
|---|---|---|
| PMDDataSource | primary key, foreign key | Char(10) |
| ImageID | primary key, foreign key | Char(10) |
| IntSummMethodID | primary key, foreign key | Char(10) |

FIG. 7F

TranscriptAbun Table

| HybID | primary key, foreign key | Char(10) |
|---|---|---|
| PMDDataSource | primary key, foreign key | Char(10) |
| ImageID | primary key, foreign key | Char(10) |
| SummaryElementID | primary key, foreign key | int |
| IntSummMethodID | primary key, foreign key | Char(10) |
| AbunCalcMethodID | primary key, foreign key | Char(10) |
| ArrayDesignID | foreign key | Char(10) |
| TechnologyType | foreign key | Char(10) |
| ArrayPMDDataSource | foreign key | Char(10) |
| TranscriptAbundance | | Float |
| PresenceIndicator | | Char(1) |
| AbunCalcError | | Float |

AbunCalcMethod Table

| AbunCalcMethodID | primary key | Char(10) |
|---|---|---|
| AbunCalcDescription | | Char(80) |

NormalizedImage table

| HybID | primary key, foreign key | Char(10) |
|---|---|---|
| PMDDataSource | primary key, foreign key | Char(10) |
| ImageID | primary key, foreign key | Char(10) |
| IntSummMethodID | primary key, foreign key | Char(10) |
| AbunCalcMethodID | primary key, foreign key | Char(10) |

FIG. 7G

92 Transcript Tables

Transcript Table

| TranscriptID | primary key | Char(15) |
|---|---|---|
| PMDDataSource | foreign key | Char(10) |
| TranscriptDescription | | Char(80) |
| MfgID | | Char(25) |
| DisplayedName | | Char(20) |
| HitID | | Char(8) |
| HitType | | Char(1) |
| HitDataSource | | Char(10) |
| HitDescriptionShort | | Char(40) |
| HitScore | | integer |
| CloneID | | Char(10) |
| InternalID | | Char(20) |

ExternalHit Table

| HitID | primary key | Char(8) |
|---|---|---|
| HitType | primary key | Char(1) |
| CommonGene | | Char(1) |
| HitDescription | | Char(255) |
| HitDataSource | | Char(10) |

ProteinFunction Table

| PFID | primary key | Char(38) |
|---|---|---|
| PFType | | Char(1) |
| PFFullID | | Char(38) |
| PFDescription | | Char(150) |

*FIG. 7H*

PFExternalHit

| HitID | primary key | Char(8) |
|---|---|---|
| HitType | primary key | Char(1) |
| PFID | primary key | Char(38) |

FIG. 71

88 Sample Tables
Sample Table

| SampleID | primary key | Char(10) |
|---|---|---|
| PMDDataSource | primary key, foreign key | Char(10) |
| TissueCategory | | Char(40) |
| SampleDescription | | Char(80) |

TissueSample Table

| TissueID | primary key, foreign key | int |
|---|---|---|
| SampleID | primary key, foreign key | Char(10) |
| PMDDataSource | primary key, foreign key | Char(10) |

SamplePrepSample Table

| SampleID | primary key, foreign key | Char(10) |
|---|---|---|
| PMDDataSource | primary key, foreign key | Char(10) |
| PrepSampleID | primary key, foreign key | Char(10) |

FIG. 7J

PrepSample Table

| PrepSampleID | primary key | Char(10) |
|---|---|---|
| PMDDataSource | primary key, foreign key | Char(10) |
| PrepSample Description | | Char(80) |
| LabelType | foreign key | Char(15) |
| TranscriptionMethodID | foreign key | Char(10) |
| ProtocolID | foreign key | Char(10) |

Protocol Table

| ProtocolID | primary key | Char(10) |
|---|---|---|
| ProtocolDescription | | Char(40) |

TranscriptionMethod Table

| TranscriptMethodID | primary key | Char(10) |
|---|---|---|
| TranscriptionDescription | | Char(40) |

PrepSampleControl Table

| PrepSampleID | primary key, foreign key | Char(10) |
|---|---|---|
| PMDDataSource | primary key, foreign key | Char(10) |
| ControlID | primary key, foreign key | Char(10) |
| Concentration | | Float |
| Unit | | Char(10) |

Control Table

| ControlID | primary key | Char(10) |
|---|---|---|
| ControlDescription | | Char(40) |

FIG. 7K

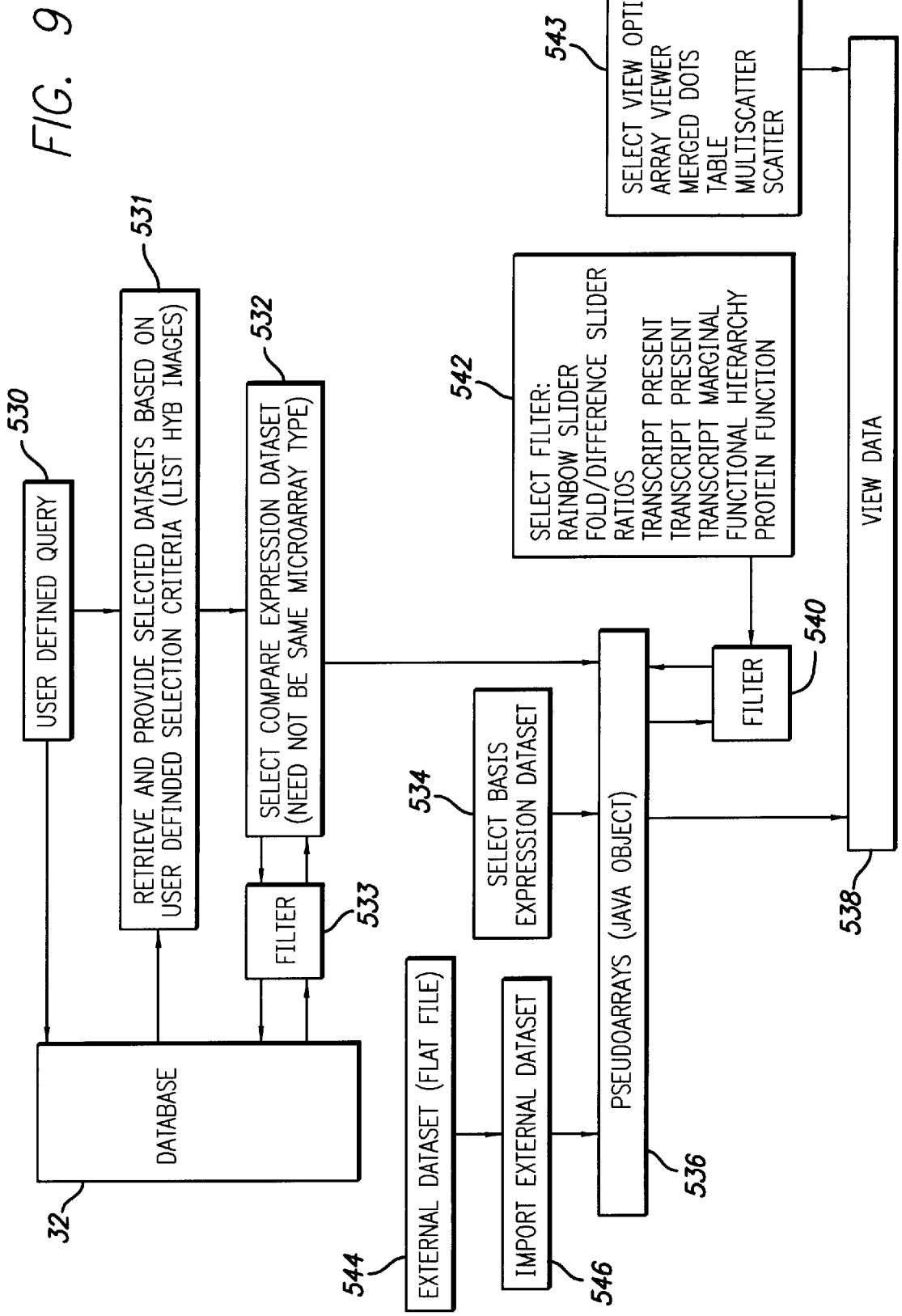

Transcript Abundance Information — 690

| | |
|---|---|
| Hyb ID: | HYB-1 |
| Image ID: | IMAGE01 |
| PMD Data Source: | INCYTE |
| Technology Type: | Technology |
| | |
| Abun CalcMethod: | Unnormalized Data |
| Summarization Method: | Incyte Method |
| | |
| HitID: | g178746 |
| Hit Description: | Human apurinic/apyrimidinic endonuclease |
| | |
| Summary Element ID: | 44 |
| Transcript Abundance: | 2390.00 |
| Abun Calc Error: | 0.000 |
| Summarized Intensity: | 2390 |
| Summarization Error: | 0.000 |

FIG. 13A

Hybridization Information

| Hyb Name | Technology Type | Prep Sample | Clone ID |
|---|---|---|---|
| Hyb 1 | type 1 | demo 1 | I0004 |
| Hyb 2 | type 2 | demo 2 | I123456 |

| Hyb Name | HitID | Hit Description |
|---|---|---|
| Hyb 1 | g12345 | gene1 |
| Hyb 2 | g23445 | gene2 |

SYSTEM AND METHOD FOR GENERATING, ANALYZING AND STORING NORMALIZED EXPRESSION DATASETS FROM RAW EXPRESSION DATASETS DERIVED FROM MICROARRAY INCLUDES NUCLEIC ACID PROBE SEQUENCES

The present application claims priority to U.S. Provisional Patent Application Serial No. 60/073,045, entitled BIOLOGICAL MICROARRAY DATABASE AND SYSTEM, filed Jan. 29, 1998, and to United States Provisional Patent Application Serial No. 60/079,094 entitled BIOLOGICAL MICROARRAY DATABASE AND SYSTEM II, filed Mar. 23, 1998, both of which are incorporated by reference herein for all purposes.

The present invention relates generally to systems and databases for obtaining, storing and retrieving biomolecular information. More particularly, the invention relates to a system and method for generating, storing and providing information relating to biomolecular data in a relational database.

BACKGROUND OF THE INVENTION

Gene expression data analysis serves to identify genes which may be employed as markers for a particular disease or may be selected as gene targets for the development of new pharmaceutical compounds. Additionally, gene expression analysis can provide insight into the interactions between a large number of genes, including whether two or more genes belong to a common regulatory pathway.

Microarray-based experiments are presently a preferred method to generate gene expression data. Microarrays consist of an ordered arrangement of known gene sequences, or array elements, immobilized on a substrate. To generate gene expression data, the array elements are probed with a sample. The sample may have been derived, for example, from tissue of an individual suffering from a disease, from tissue treated in a specified manner or a control tissue. Samples are typically prepared by isolating mRNA, or its equivalent, and then labeling the mRNA with a fluorescent reporter group. The labeled mRNA sample is then combined with microarray array elements to form hybridization complexes between array elements and mRNA molecules that have identical or similar sequences (complementary sequences). Those labeled mRNA molecules that do not have a sequence complementary to the array element sequences are removed by a series of washes. Any formed complexes are detected by using a scanner to measure fluorescent signals emitted from specific locations on the microarray. Since the position and sequence of each array element is known, microarrays are an effective way to determine which specific genes are expressed in a sample.

The microarray hybridization experiments may be performed using one of several formats. In one format, a microarray is probed using a single labeled mRNA sample and what is detected after complex formation is an absolute measurement of levels of particular mRNAs in a sample. In a second format, a microarray is probed using two mRNA samples, each labeled with a different fluorescent reporter group, at the same time. In this case, the mRNAs from the two samples compete for hybridization to individual array elements and a ratio which reflects the relative abundances of a gene in the different samples is obtained. Typically, the competitive hybridization format is more reliable than the absolute hybridization format where comparisons of gene transcript levels has to be performed across more than one microarray.

Microarray-based experiments are generating increasing volumes of gene expression information which needs to be generated, stored and provided in an effective manner. The present invention provides the necessary software tools for the generation, storage and retrieval of such information. The software tools can be used to analyze data in both absolute and competitive hybridization formats.

SUMMARY OF THE INVENTION

In one embodiment, a biomolecular expression information processing system has procedures and tables that store hybridization data and abundance datasets. The hybridization data comprises information describing a sample and a microarray to which the sample is applied. The hybridization data also comprises information on expression data or levels from which the abundance dataset is generated. The tables also store information identifying a microarray technology type for each hybridization and microarray design information for each microarray technology type. The microarray design information includes technology data that specifies global characteristics of each microarray, and array element data that specifies characteristics, such as location and sequence information, of array elements in each microarray instance of the microarray technology type. The procedures process the abundance datasets in accordance with the microarray design information associated with each such abundance dataset. The system stores technology data for multiple distinct microarray technology types and stores array element data for multiple microarray designs of a single technology type.

When the biomolecules are genetic sequences, hybridizations are used to determine expression data or levels. When the biomolecules are polypeptide sequences, antibodies are used to determine expression data or levels.

In another embodiment, the biomolecular expression information processing system stores expression data for polypeptide sequences that was generated by the microarrays using antibodies.

BRIEF DESCRIPTION OF THE DRAWINGS

Additional objects and features of the invention will be more readily apparent from the following detailed description and appended claims when taken in conjunction with the drawings, in which:

FIGS. 7A to 7K depict a data model for the expression database.

FIG. 9 is a block diagram illustrating the generation of pseudoarrays by a user.

FIGS. 13A and 13B depict two-types of exemplary drill-down windows for displaying detailed information about an element of interest.

DESCRIPTION OF THE PREFERRED EMBODIMENTS

Figure 1:
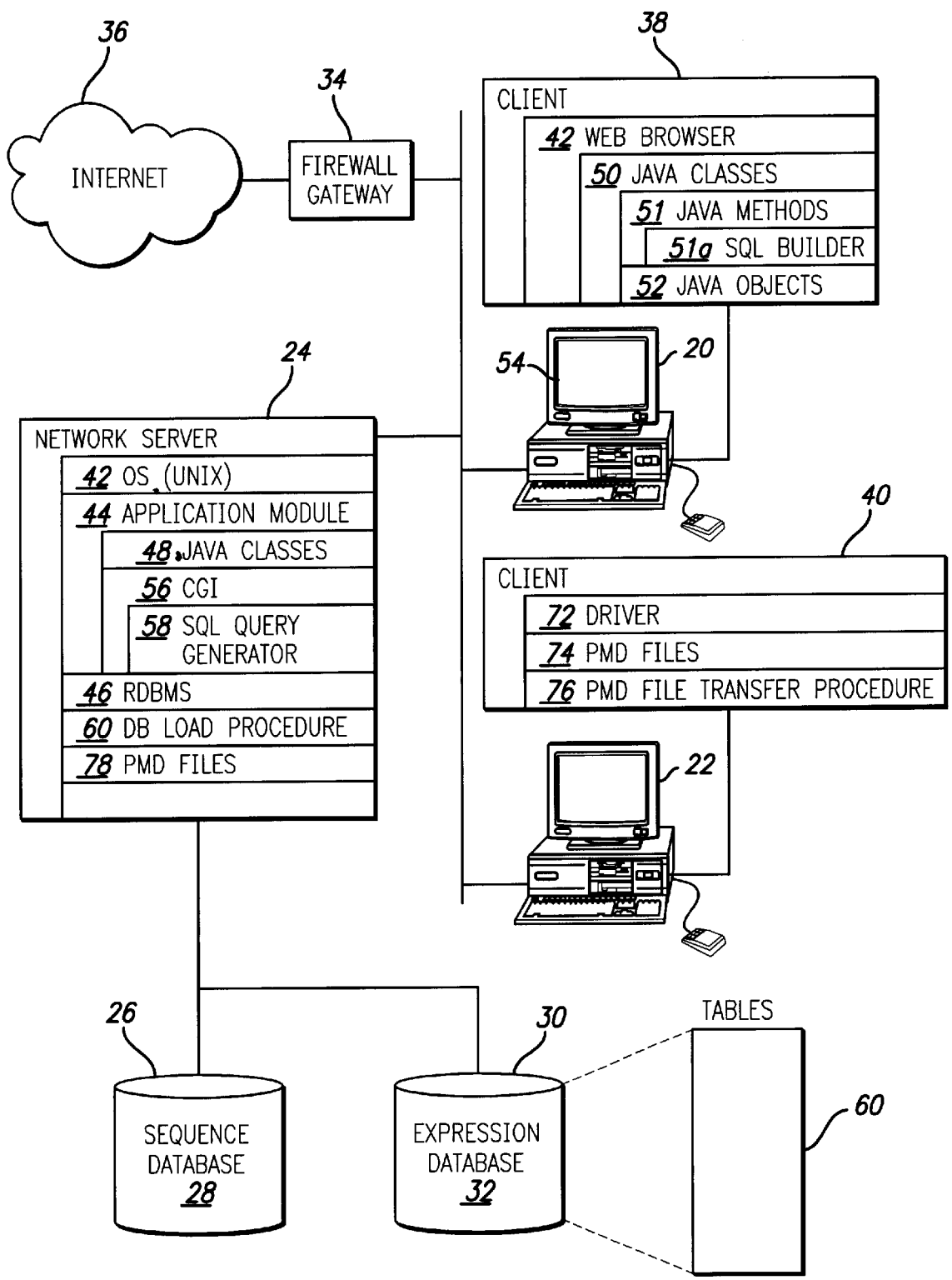
FIG. 1 is a diagram of a client-server system suitable for use with the present invention.

FIG. 1 depicts a network system for retrieving information stored in the biomolecular expression information processing system of the present invention. The major computer system components of the network are:

at least one client computer system 20, 22, at least one network server 24 a storage device 26 storing a sequence database 28 another storage device 30 storing a biomolecular expression database 32, and a firewall gateway server 34 that connects to the Internet 36.

FIG. 1 depicts the memories 38 and 40 of the client computers 20 and 22 respectively. On the client computer system 20, a user runs web browser software 42 such as Netscape.

The network server 24 has a UNIX operating system 43, an application software module 44 and a relational database management system (RDBMS) 46 such as Oracle. When a user first accesses the application module 44 via the web browser 42, the application module 44 uploads JAVA classes 48 from the server 24 to the client system 20. The Web Browser 42 executes the uploaded JAVA classes 50 which use JAVA objects 52 to provide a graphical user interface 54 to the application module 44 for the user. At startup, a subset of the JAVA objects are loaded with data from the database.

To retrieve data from the expression database 32, methods 51 within JAVA classes 50, such as a SQL builder 51 a, on client 20 build a SQL statement based on user defined criteria that is passed to a CGI 56 on the network server 24. The CGI 56 then passes this to the RDBMS 46. The RDBMS 46 executes the SQL statement and returns the retrieved data to the CGI 56 which, in turn, passes the data back to the client 20. The JAVA classes populate the JAVA objects 52 with the retrieved data.

In an alternate method of retrieving data from the database, methods within the JAVA classes 50 pass a parameter to the CGI script 56 which builds a SQL statement using a SQL Query Generator 58. The SQL statement is passed to the RDBMS.

The expression database 32 is stored on storage media in a storage device such as a disk drive. In particular, the expression database 32 stores the data in tables 60.

The client systems 20, 22, also access public domain resources on the Internet 36 via the firewall gateway server 34. The client systems 20, 22, network server 24 and the firewall gateway server 34 are networked via an intranet using TCP/IP protocol.

One of the client systems 22 generates the data that is loaded in the expression database 32. A driver module 72 receives raw expression data and processes the raw expression data into flat files having a predetermined format, called PMD files 74. After generating the PMD files 74, a PMD file transfer procedure 76 is run to transfer or copy the PMD files 76 and 78 to the network server 24. Once on the network server 24, a database load procedure 80 is executed which interacts with the RDBMS 46 to load the data in the PMD files 78 into the tables 60 of the expression database 32.

Figure 2:
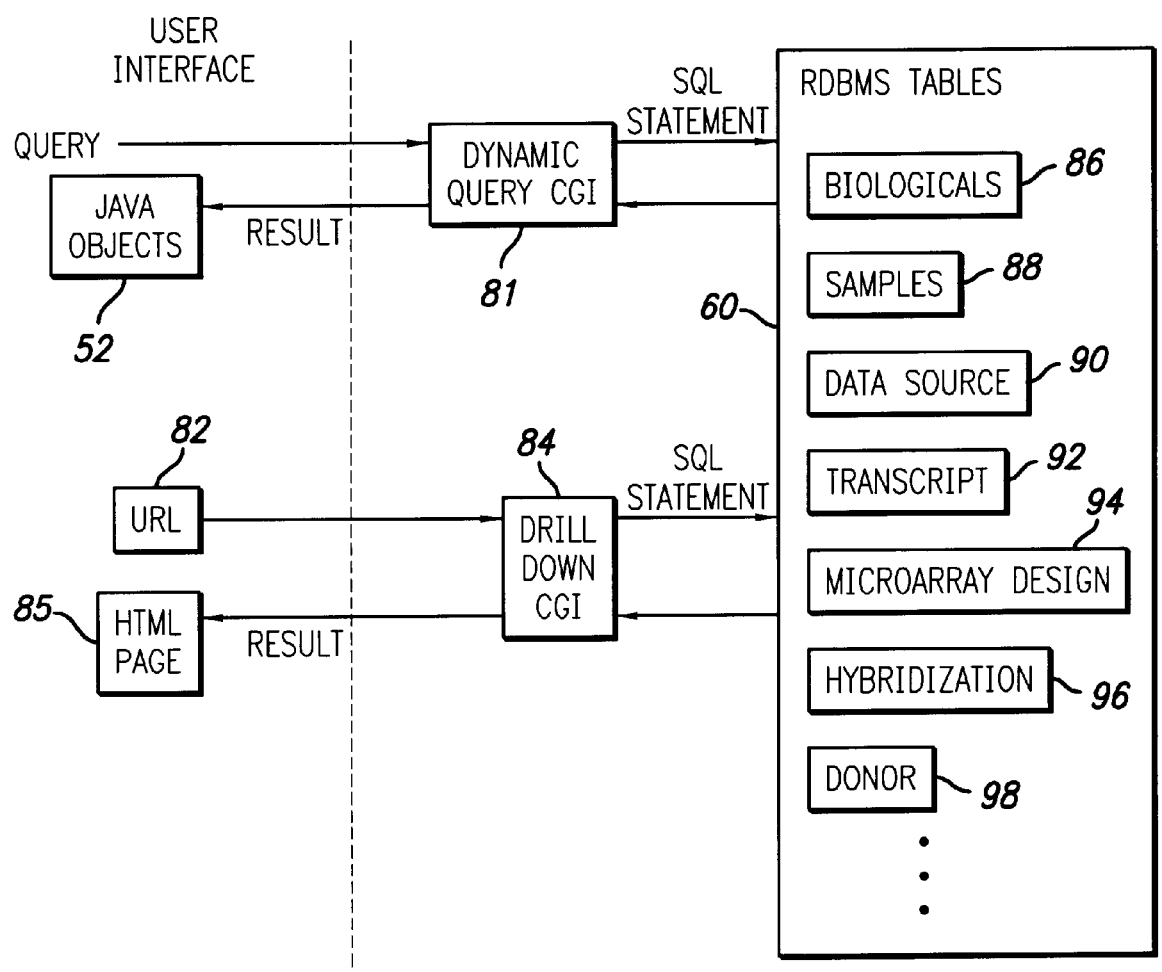
FIG. 2 is a data flow diagram of a query to the result that is displayed on the user interface.

FIG. 2 illustrates the flow of a database query from the user interface. The graphical user interface 54 allows the user to graphically construct search requests to retrieve data from the tables 60 of the expression database. The commands of the search request are called queries. As described above, either the JAVA classes or the CGI scripts generate the database queries. The JAVA classes generate the SQL statement and pass that statement to a dynamic query CGI 81 which passes the SQL statement to the RDBMS to access data from the tables 60. The RDBMS returns the data to the dynamic query CGI 81 which then passes the data to the JAVA classes 50 that in turn populate the JAVA objects 52, and the results are displayed on the GUI 54 on the client computer 20.

Alternately, the JAVA classes pass a URL 82 to a drill down CGI 84. The URL designates a particular CGI 84 and specifies one or more parameters. Based on the parameters, the particular drill down CGI 84 generates a SQL statement which is executed by the RDBMS to access the data from the tables 60 and returns the data to the drill down CGI 84. The drill down CGI script 84 generates an HTML page 85 and displays the data to the user on the client 20 in the HTML page 85.

The expression database 32 has many tables 60 storing information including biologicals 86, samples 88, data source 90, transcript 92, microarray design 94 hybridization 96, donor 98 and the like.

Figure 3:
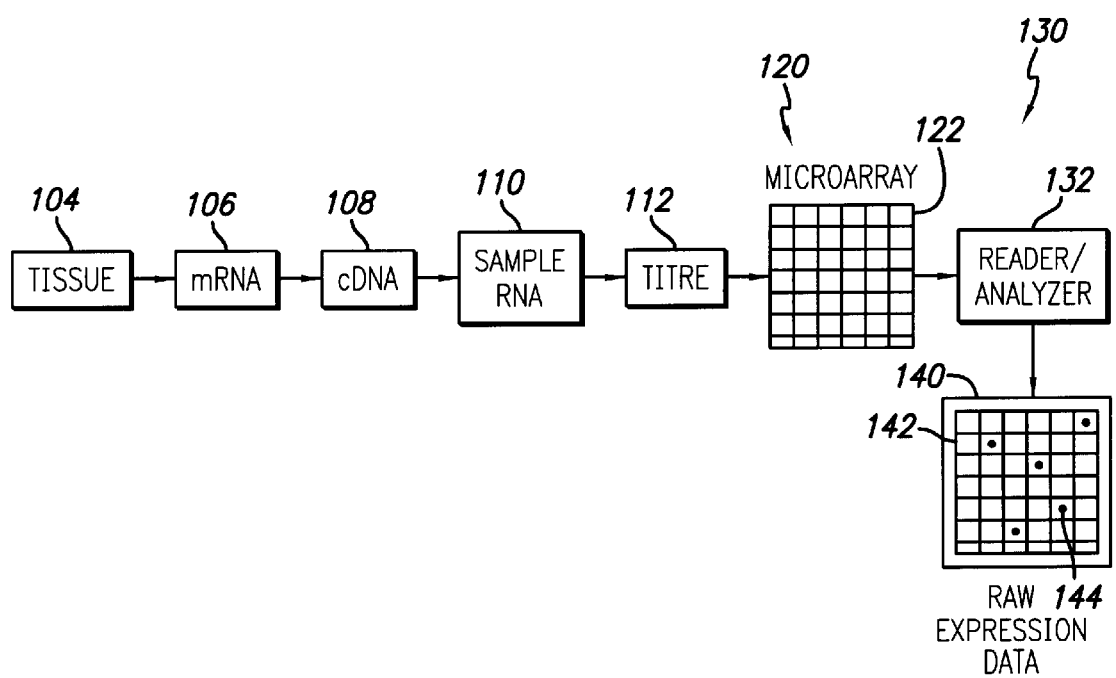
FIG. 3 illustrates a method of generating the raw image data for a sample from a microarray.

FIG. 3 illustrates a method of generating the raw expression data for a sample from a microarray. Microarrays are composed of nucleic acid probe sequences representing a number of genes or gene fragments. For example, the gene sequences may have a common association, such as a common tissue or organ system, a common biological functionality or common disease state, or may reflect all the genes of an organism such as a human, animal, plant or bacterium.

Generally, a microarray manufacturer provides data on the specific transcripts represented on the microarray and identifies the site or sites on the microarray having probes corresponding to a particular transcript. Different manufacturers use different microarray fabrication technologies. For example, one type of microarray technology is capable of providing probes for up to about 10,000 genes on a 1 $cm^2$ surface.

A hybridization is an individual application of a sample to a microarray. In a hybridization, information is obtained on expression data or levels as reflected by observed expression intensities. Typically, there are two types of samples: control samples and test samples. Control samples are based on mRNA from healthy individuals or untreated donor tissue. Test samples are based on mRNA from tissue from an individual suffering from a disease or which has been treated with a particular drug or other agent.

An experiment refers to the application of a set of control and treated samples from the same donor tissue to a particular microarray design. An experiment has one or more hybridizations. Data on each sample, hybridization and experiment is loaded into the database. In a hybridization experiment, control and treated samples are applied to separate microarrays of the same microarray design to compare the resulting data. Alternately, some types of microarrays have both the control and the test samples applied to the same microarray.

The microarray design includes a set of data which is loaded into the database to aid in the analysis of the results of the experiments conducted with the microarray.

In FIG. 3, sample 104, such as a tissue sample, is acquired from a donor. The sample is prepared by isolating the mRNA (106). The mRNA is labeled with a fluorescent marker (108). This may be achieved by reverse transcribing the mRNA to cDNA using the enzyme reverse transcriptase, then in step 110 transcribing the cDNA to RNA in vitro in the presence of one or more fluorescently labeled ribonucleotides using T7 RNA-transcriptase. In step 112, the RNA sample is divided and diluted into the appropriate size and concentration (titre). In step 120, the titre is applied to the microarray 122 in a hybridization.

In step 130, a microarray reader/analyzer 132 analyzes the prepared microarray 122. Typically, microarrays 122 are used with proprietary hardware and software for running the hybridization experiments and the microarray reader/analyzer outputs raw expression data (140) for each site or element 142. The raw expression data 140 includes fluorescence intensity values for each element 142 on the microarray. In the exemplary raw expression data 140, the black dots 144 indicate that those elements have high intensity values.

Other microarray systems further analyze the raw expression data and provide, in addition to the raw expression data 140, a determination of expression or non-expression such as a ratio. In addition, the level of any expression can alternately be based on hybridization data collected over several different sites having different probes associated with a given gene. The raw expression data 140 that is output from each manufacturer's reader/analyzer also has a data format particular for their own system. The reader/analyzer also supplies user defined data 142 in either a separate file or alternately in the same file with the raw expression data 140. The user defined data includes the genes and transcripts represented on the microarray and their location, microarray design information, donor information, biological information, data source, sample information, descriptions of the experimental samples and additional experimental data, and hybridization information.

Note that for microarrays using competitive hybridization, the reader/analyzer generates a set of raw expression data for each individual sample, each of which has been marked with a different fluorescent marker.

Figure 4A:
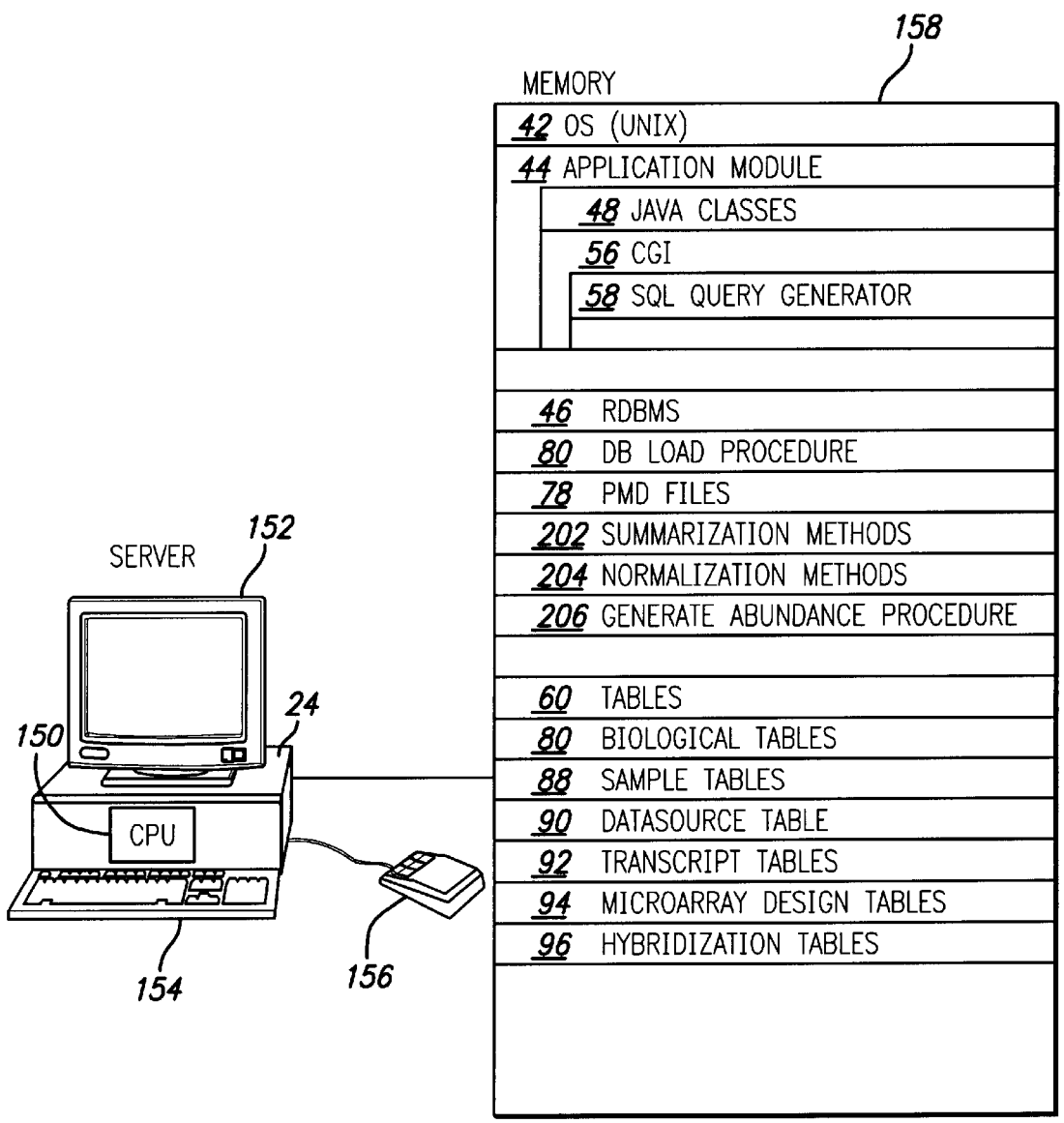
FIG. 4A shows exemplary procedures and data stored in the memory of the network computer system.
Figure 4B:
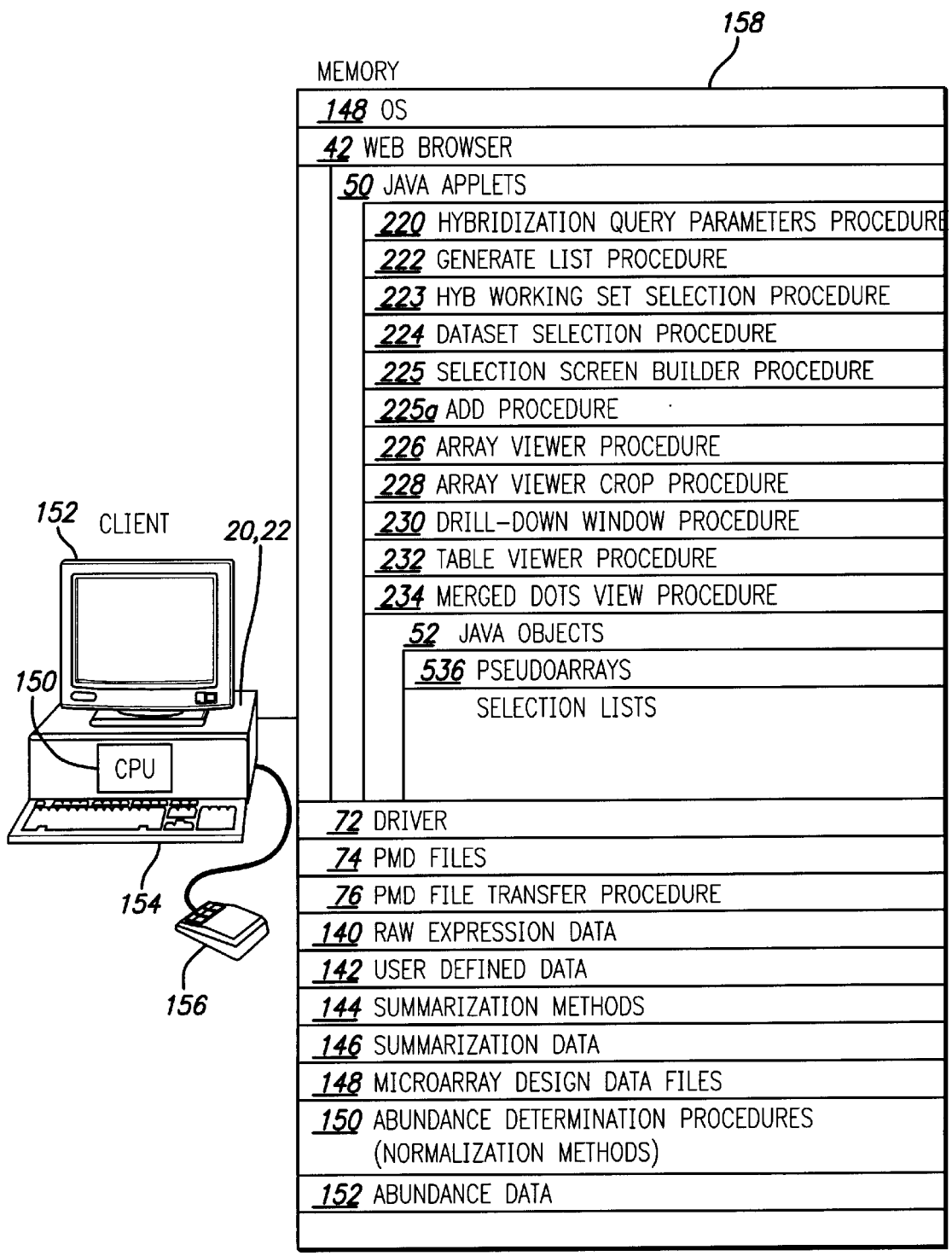
FIG. 4B shows exemplary procedures and data stored in the memory of an exemplary client computer system.

FIGS. 4A and 4B shows exemplary procedures and data stored in the memory of the network 24 and client computer systems 20, 22, respectively. Each system has a CPU 150, display 152, keyboard 154, mouse 156 and memory 158. The memory 158 includes RAM and various storage devices including disk drives. The procedures are numbered and will be described below.

Figure 5:
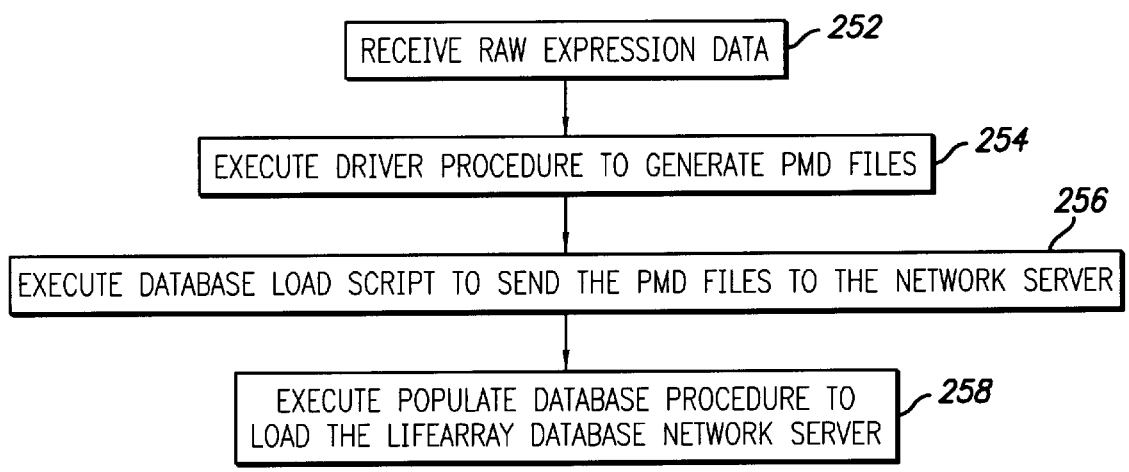
FIG. 5 illustrates the steps of loading the raw image into the database of the present invention.

FIG. 5 illustrates the steps of loading the raw expression data 140 into the expression database 32. In step 252, one of the client systems receives the raw expression data 140 (FIG. 4B) from the microarray reader/analyzer in the form of a file. In step 254, the system executes the driver procedure 72 (FIG. 4B) to generate flat files, called Processed MicroArray Data (PMD) files, from the raw expression data. A driver is provided for each type of microarray. The driver procedure also performs additional processing of the data which will be discussed below with reference to FIG. 6. In step 256, the client system executes the PMD file transfer procedure 76 (FIG. 4B) to transfer or copy the PMD files into the network server. In step 258, the database load procedure 80 (FIG. 4A) is executed which interacts with the RDBMS to load the PMD files into the expression database.

Figure 6:
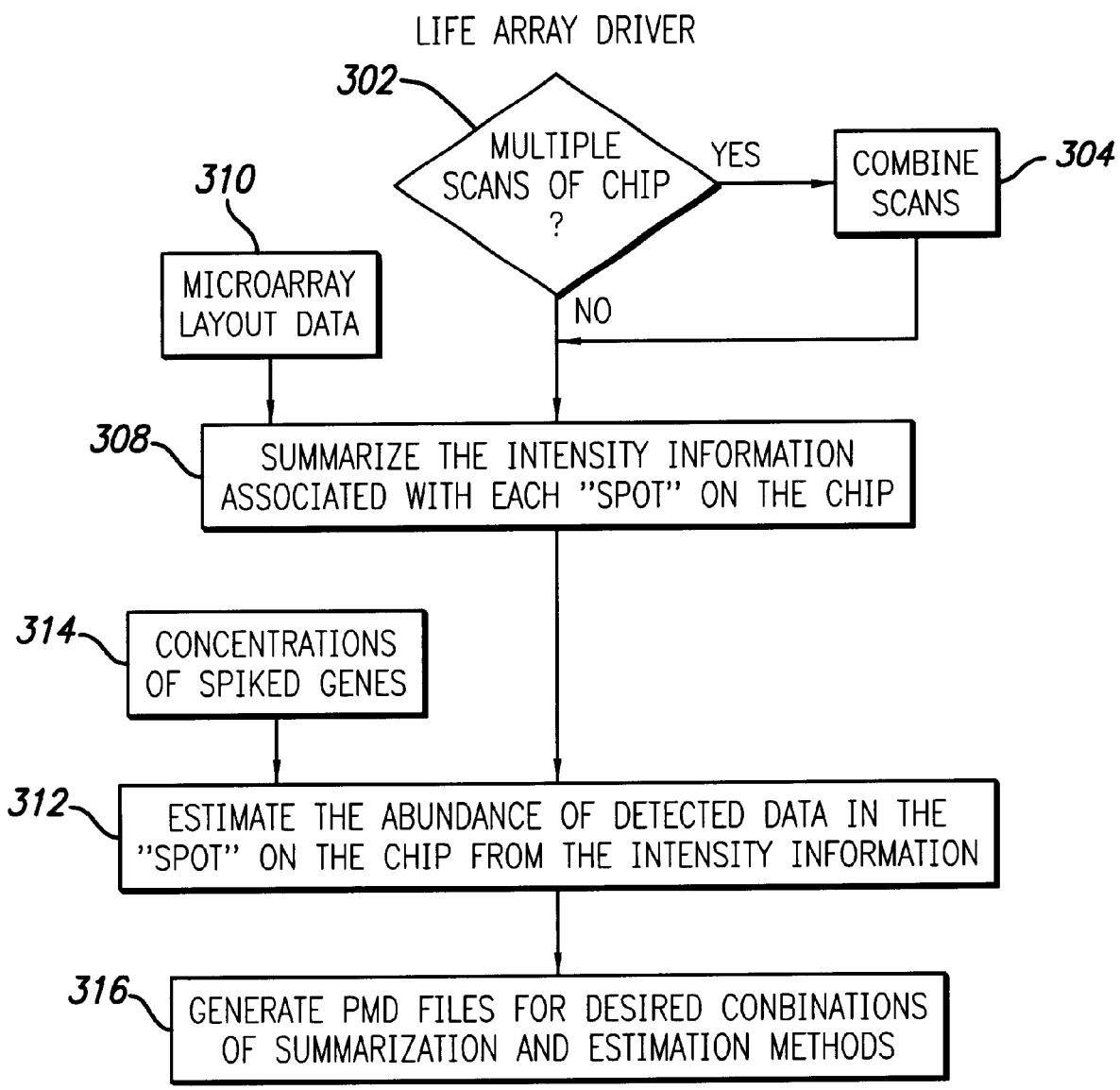
FIG. 6 is a detailed block diagram illustrating the steps involved in generating the PMD files of FIG. 5.

FIG. 6 is a detailed block diagram of the steps used to generate the PMD files of step 254 of FIG. 5. In the PMD files, the raw expression data is organized together with other user defined data 142 (FIG. 4B) into a format suitable for loading into the expression database.

Step 302 determines if the microarray reader/analyzer performed multiple scans of the microarray. If so, step 304 combines the expression data from those scans to create a single expression file storing, for example, the average intensity at each spot or element on the array. If no multiple scans were performed, step 308 executes the summarization method or procedure 144 (FIG. 4B) that summarizes the intensity information associated with each element of the microarray to generate summarization data 146 (FIG. 4B). To correlate the elements on the microarray with the probe design in the summarization method, step 310 provides microarray layout data to the summarization method using microarray design data files 148 (FIG. 4B). In particular, one summarization method averages all fluorescence intensity values associated with a particular gene or element on the microarray. Other methods summarize by eliminating intensity values above and below predefined high and low thresholds, respectively, and averaging the remaining intensity values. In some cases, depending on the microarray technology, summarization is not performed.

In step 312, an abundance determination procedure 150 (FIG. 4B) generates abundance data 152 (FIG. 4B) for the elements based on the intensity information of the summarized data. The abundance determination procedure is also referred to as a normalization method. For example, in one normalization method, the summarized intensity of an element is compared to intensity values for one or more elements that were spiked in known concentrations (step 314). An absolute abundance value is assigned to the element of interest based on its intensity relative to the elements of known intensity and abundance. Alternately, other normalization methods provide relative abundance values such as:

the summarized intensity per element divided by the average summarized intensity of all elements on the microarray, the summarized intensity per element over all non-control elements on the microarray, or the summarized intensity per element over the average summarized intensity of all housekeeping genes on the microarray. Housekeeping genes are those genes typically present in all cells.

In step 316, the generated abundance data from various combinations of summarization and estimation procedures is stored and formatted into the PMD files. Preferably, abundance data is generated and stored for each possible combination of summarization and normalization methods.

Structure of the Database

FIGS. 7A through 7K depict a data model for a representative set of tables and fields of the expression database 32 of the present invention. Each table is represented by a block with the name of the table listed above the block such as "PMDDataSource table." The tables store records. The table stores data for each record in the fields which are listed below each table name. The field name also describes the information stored in the field. For additional on certain fields see Table 1 below. Some fields are designated as "key" fields and those fields are underlined. There are two types of keys: primary keys and foreign keys. A primary key or a combination of primary key fields in a table is used to uniquely identify a record stored in that table. Foreign keys are used, either alone or with at least a subset of other fields in the table, to access other tables in the database.

A JOIN is a relational operation that allows a program to retrieve data from two or more tables based on matching field values. In the database, some of the key fields, both primary and foreign, are common to other tables. These common fields are used to access the data stored in the tables, and to associate or combine data from different tables in database JOIN operations. The database has a sufficient number of keys to link the data stored in the tables.

The data type is also shown. The data types are integer (int), character (char) followed by the number of characters in parentheses and floating point (float). The data type "NUMBER(8)" is a real number and the 8 means the number of digits.

FIG. 7A is the table storing the PMDDataSource information. FIG. 7B shows a representative set of tables and fields storing donor and tissue information. FIG. 7C shows a representative set of tables and fields storing microarray design information. FIGS. 7D throug 7G show a representative set of tables and fields storing hybridization information. FIGS. 7H and 7I show a representative set of tables and fields storing transcript information. FIGS. 7J and 7K show a representative set of tables and fields storing sample information.

In FIG. 7A, a PMDDataSource table 90 has a PMDDataSource field that serves as a primary key to the table, and a PMDDataSourceDescription field that stores the user's description of the data source loaded in the database. For example, the user may put their company name in this field. Since the PMDDataSource table has a single primary key, each record is unique; that is, multiple records do not use the same values for the primary key.

In FIG. 7C, the microarray design tables 94 store information relating to the microarrays. For example, the MicroarrayDesign table has a PMDDataSource field that is designated as both a primary key and a foreign key in that table. Since PMDDataSource is designated as a foreign key, that field can be used to link to the PMDDataSource table described above to associate or combine the PMDDataSourceDescription with the MicroarrayDesign table. An exemplary pseudo-SQL statement that performs a JOIN between the PMDDataSource Table and the MicroarrayDesign Table would appear as follows:

SELECT MicroArrayDesign.ArrayDesignID,
       MicroArrayDesign.TechnologyType,
       PMD DataSource. PMDDataSourceDescription,
       MicroArrayDesign. NumArrayElements
    FROM MicroArrayDesign, PMDDataSource
    WHERE MicroArrayDesign.PMDDataSource=
       PMDDataSource.PMDDataSource.

In FIGS. 7D, 7E, 7F and 7G, hybridization data is stored in many tables. Exemplary hybridization tables, shown in FIG. 7G, will now be described. Each hybridization is associated with a HybID. Those microarrays that use competitive hybridization are capable of generating more than one set of raw image or expression data. Each set of raw image data of that hybridization (HybID) is associated with a unique Image Identifier (ImageID). For example, one type of microarray using competitive hybridization that generates two images, has one Hybridization record for each of the two images, and that one Hybridization record is associated with two different image identifier values in the ImageID field.

An example of retrieving data will be described. The TranscriptAbun table stores the transcript abundance for the elements. The transcript abundance is the generated intensity value after the summarization and normalization methods are applied to the raw expression intensity data. For example, to retrieve the transcript abundance for element three from a desired image of a hybridization, the following pseudo-SQL statement would be used:

SELECT TranscriptAbun.TranscriptAbundance
    FROM TranscriptAbun
    WHERE TranscriptAbun.HybID='Hyb 1'
       AND TranscriptAbun.PMDDataSource='Synteni'
       AND TranscriptAbun.ImageID='IMAGE-1'
       AND TranscriptAbun.SummaryElementID='3'
       AND TranscriptAbun.IntSummMethodID='Summ_1'
       AND TranscriptAbun.AbundCalcMethodID='Norm_3'

The following pseudo-SQL statement retrieves the entire set of transcript abundance values for an image of a hybridization:

SELECT TranscriptAbun.TranscriptAbundance
    FROM TranscriptAbun
    WHERE TranscriptAbun.HybID='Hyb 1'
       AND TranscriptAbun.PMDDataSource='Synteni'
       AND TranscriptAbun.ImageID='IMAGE-1'
       AND TranscriptAbun.IntSummMethodID='Summ_1'
       AND TranscriptAbun.AbundCalcMethodID='Norm_3'

Note that no SummaryElementID is specified.

Assuming that the previous pseudo-SQL statement retrieved a first set of data from a competitive hybridization generated by a first fluorescent marker, then the following SQL statement retrieves a second set of data for the second fluorescent marker:

SELECT TranscriptAbun.TranscriptAbundance
    FROM TranscriptAbun
    WHERE TranscriptAbun.HybID='Hyb 1'
    AND TranscriptAbun.PMDDataSource='Synteni'
    AND TranscriptAbun.ImageID='IMAGE-2'
    AND TranscriptAbun.IntSummMethodID='Summ_1'
    AND TranscriptAbun.AbunCalcMethodID='Norm_3'

The following pseudo-SQL statement performs a JOIN between the TranscriptAbun table and the SummaryArrayElement Table to retrieves the entire set of transcript abundance values for an image of a hybridization, and the corresponding SummaryRow and SummaryColumn data from the SummaryArrayElement Table:

SELECT
    TranscriptAbun.TranscriptAbundance, SummaryArrayElement. SummaryRow,
       SummaryArrayElement.SummaryCol
    FROM TranscriptAbun,SummaryArrayElement
    WHERE TranscriptAbun.HybID='Hyb 1'
       AND TranscriptAbun.PMDDataSource='Sinteni'
       AND TranscriptAbun.ImageID='IMAGE-1'
       AND TranscriptAbun.IntSummMethodID='Summ_1'
       AND TranscriptAbun.AbunCalcMethodID='Norm_3'
       AND SummaryArrayElement.ArrayDesignID=
          TranscriptAbun.ArrayDesignID
       AND SummaryArrayElement.PMDDataSource=
          TranscriptAbun.ArrayPMDDataSource AND SummaryArrayElement.TechnologyType= TranscriptAbun.TechnologyType AND SummaryArrayElement.SummaryElementID= TranscriptAbun.SummaryElementID Note that two data sources, the PMDDataSource and the ArrayPMDDataSource, allow two different data sources to be specified. For example, in a company in which one group designs the microarray and another group runs the hybridization, each group is designated with a different PMDDataSource, such as "Group 1" and "Group 2." The TranscriptAbun Table stores both the PMDDataSource and the ArrayPMDDataSource as primary and foreign key fields, respectively. Therefore, the source of the data for the array design and the source of the data for the hybridization are both identified and stored.

Similarly, using the primary and foreign keys, all tables of the database are associated with or joined with each other to retrieve the selected data.

A dataset refers to a set or collection of related data. For example, in the expression database, the raw expression data from a microarray is stored as a dataset. The data of the dataset is stored in many tables. Alternately, the data of a dataset is stored in a single table. A dataset is also the result of a SQL select or join operation. Similarly, the summarization data and abundance data are also stored as datasets. An abundance dataset includes the summarized and normalized intensity values associated with the elements of the microarray.

Method identifiers representing the summarization and normalization methods that were used to generate the summarization and abundance datasets are also stored in the database. In particular, a summarization method identifier, called Summary MethodID is stored in the Summarized Table to associate the summarized intensity values with a particular summarization method. An AbunCalcMethodID is used to identify a particular normalization method that generated the abundance data. The Summary MethodID and the AbunCalcMethod ID are both stored in the TranscriptAbun table to associate the generated abundance intensity values with the summarization and normalization methods that generated the data. In the TranscriptAbun Table, both the Summary MethodID and the AbunCalcMethod ID are designated as primary keys. In this manner, two distinct abundance datasets corresponding to a single raw expression dataset are stored.

In addition, the database stores hybridization data that identifies, for at least a subset of the abundance datasets, a hybridization from which the abundance dataset was generated. A hybridization includes a sample and microarray to which the sample was applied. In the hybridization tables, an image identifier (ImageID) field identifies a particular stored image or scan for that hybridization. The image identifier (ImageID), in conjunction with the hybridization identifier (HyBID), allows the database to store one or more sets of raw expression data for a single hybridization. Therefore, the database stores data for microarrays that use either absolute and/or competitive hybridization. The intensity values for the raw expression data are stored in the Intensity field of the ImageDetail Table (FIG. 7E).

The database stores information identifying a microarray design of a technology type for each hybridization in the Summarizedintensity Table and the Abundance table. In particular, in these tables, the technology type is a key field that is used to access the TechnologyDescription information stored in the Technology Table, discussed below.

The database stores microarray design information for each microarray technology type that includes technology and array element data. The technology data specifies global characteristics of each microarray instance of the microarray technology type. For example, one portion of the technology data called the technology type and a corresponding description is stored in the Technology Table. Additional design data of a technology is stored in the Design Table such as design name and the number of array elements (NumArray Elements) with the key fields as shown in FIG. 7C. A SummaryArrayElement Table stores the physical row and column information for each summary element identifier (SummaryElementID).

The array element data specifies characteristics of array elements in each microarray instance of the microarray technology type. For example, in the SummaryArrayElement Table, a transcript ID, concentration, unit, control transcript YN field, Sequence ID, the summary row and the summary column locations are stored for each element. The MicroarrayDesign table stores the array design name, purpose, number of elements and comments.

The system also stores information relating to the sample applied including a description of the sample and any treatment, the tissue category, and control information if applicable. In addition, the tables store information about the donor of the sample such as the organ the tissue came from, age and sex.

The system stores information describing the transcripts that are being detected by a microarray design such as a transcript description, a clone identifier (clone ID), HitID and Hit Description. The clone ID or clone identifer is an "INCYTE" identifier for a gene sequence. The HitID is an identifier for a gene sequence obtained from the public domain, such as GenBank. The hit Description is the annotation or description associated with a HitID.

The biomolecular expression information processing system stores datasets in which one type of microarray technology generates a single dataset of raw expression data for a single hybridization, and another microarray technology type generates at least two datasets of raw expression data for a single hybridization.

The system executes procedures that process the abundance datasets in accordance with the microarray design information associated with each such abundance dataset. Therefore, the system is capable of storing technology data for multiple distinct microarray technology types and capable of storing array element data for multiple microarray designs of a single technology type.

In particular, the system has a dataset comparison procedure 220 (FIG. 4B) that selects one abundance dataset as a base expression dataset, selects another abundance dataset as a comparison dataset, and generates a set of expression ratio values representing ratios of expression intensities in the selected and base expression datasets.

Figure 8:
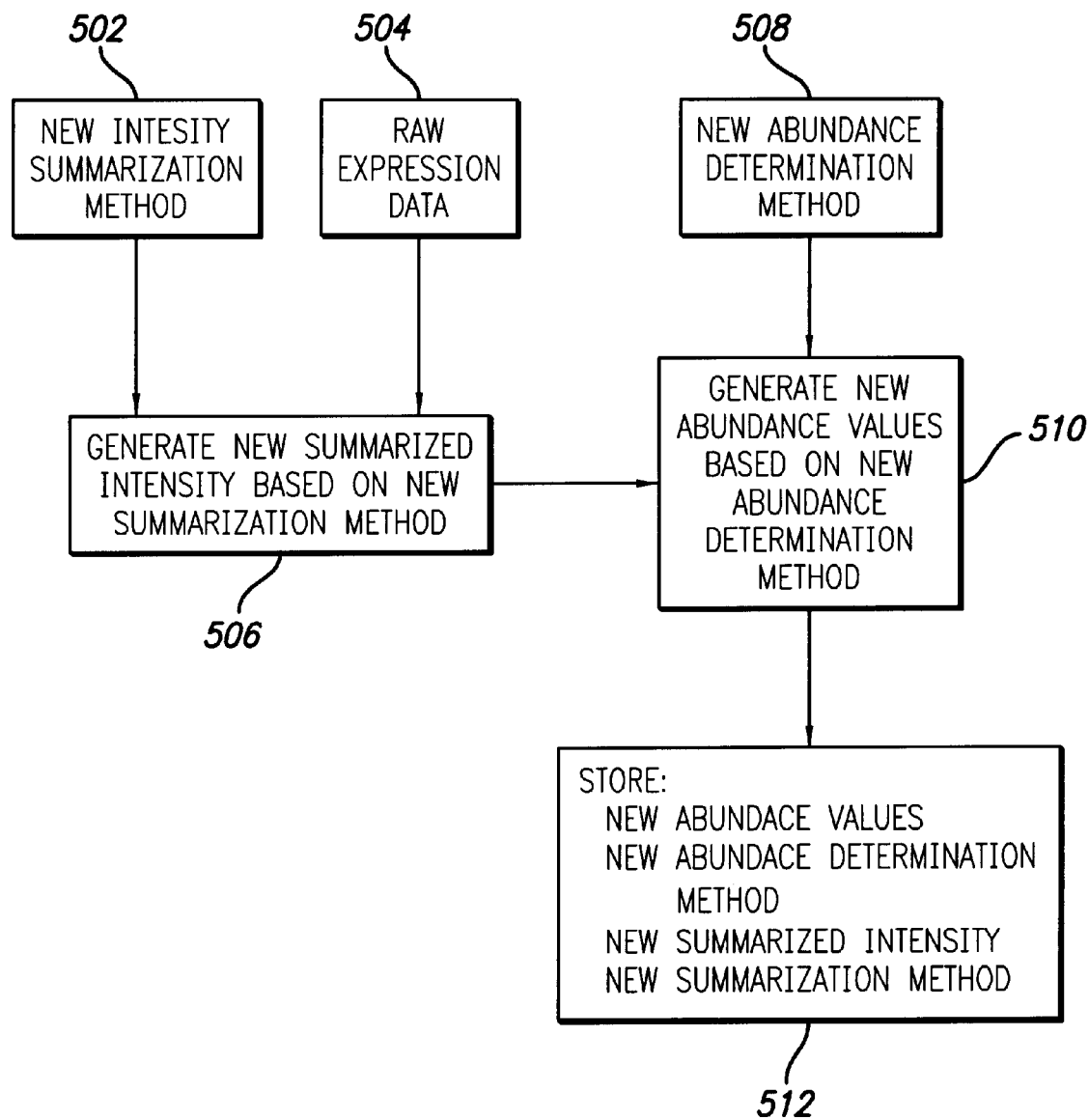
FIG. 8 is a block diagram illustrating the steps of one embodiment of the invention in which new abundance data is generated using raw expression data stored in the database and a new abundance determination procedure.

FIG. 8 is a block diagram illustrating the steps of one embodiment of the invention in which a generate abundance procedure 206 generates new abundance data using historical raw expression data stored in the database and a new abundance determination procedure. In this embodiment, the expression database also stores the summarization and normalization methods 202 and 204 (FIG. 4A) that were used to generate the abundance values. Step 502 provides a new summarization method and step 504 provides raw expression data that is stored in the database as a dataset. In step 506, new summarized intensity data is generated based on the new intensity summarization method. Step 508 provides a new abundance determination method to step 510 which generates new abundance data based on the new abundance determination method. Step 512 stores the new abundance data, new summarization data, new summarization method and new abundance determination method in the expression database.

Alternately, a new summarization method is not provided, and new abundance data is generated based on existing summarization data and the new abundance method. In another alternate embodiment, a new abundance determination method is not provided, new summarization data is generated based on the historical raw expression data and the new summarization method. New abundance data is then generated using one of the historical abundance determination methods already stored in the database.

The biomolecular information processing system allows a user to compare elements of the datasets both graphically and in tables. The user selects a set of expression datasets and each data set has elements. The user selects a subset of the elements according to specified selection criteria. The system stores the selected elements in one or more pseudoarrays. Using the pseudoarrays, the system compares corresponding elements of different selected datasets to identify biomolecular expression differences between the selected expression datasets. Even expression datasets from different microarray technologies can be compared.

FIG. 9 is a block diagram illustrating dataset selection and generation of pseudoarrays. As described above, the biomolecular information processing system uploads Java classes to the client machine to provide a graphical user interface for the user to create a query.

In step 530, a user defines a query. The biomolecular information processing system generates a JAVA applet window (FIG. 10A) displaying a query tool allowing the user to define a set of query criteria. The user-defined set of query criteria are then used to generate a SQL statement.

In step 531, a data set selection procedure 224 (FIGS. 4B and 10B) retrieves the datasets from the RDBMS based on the SQL Statement generated from the set of query criteria and populates the JAVA Objects with sufficient information to display the names of the datasets resulting from the user-defined query in a hierarchical format. In other words, the names of the datasets resulting from the user defined query are displayed.

In step 532, the user selects the particular datasets to be compared. The user selects or highlights one or more of the displayed dataset names to include in a hybridization working set (hyb working set). The hybridization working set will be used for comparisons.

A pseudoarray is a representation of a set of data describing a hybridization-image, that is, a particular image of a hybridization. The pseudoarray includes but is not limited to a set of abundance data for the hyb-image. A particular pseudoarray can include all or a subset of the abundance data for the hyb-image. The pseudoarray is implemented using JAVA objects.

The elements of a microarray have a prescribed physical layout. A pseudoarray includes one or all of the elements of the physical microarray. The elements of the pseudoarray are displayed in a user-specified configuration.

In step 536, the JAVA objects for the pseudoarrays are populated with the retrieved data. When a dataset is added to the hyb working set, the system accesses the expression database to retrieve the data associated with the individual elements of each dataset. The expression datasets need not use the same microarray technology.

An optional filter 533 is provided. If the user had defined a set of query criteria, certain of these criteria are used to filter the dataset elements retrieved when the datasets are added to the working set in step 532. The filter criteria include filtering by abundance, transcript and/or by sequence using the blast query feature. However, the invention is not meant to be limited to the previous filter criteria, in an alternate embodiment, other filter criteria are used. The filter is enabled or disabled by the user.

The user can select a basis or base dataset for the comparison (534). If the user does not select a base data set, the system designates the first retrieved dataset as the basis.

Figure 11:
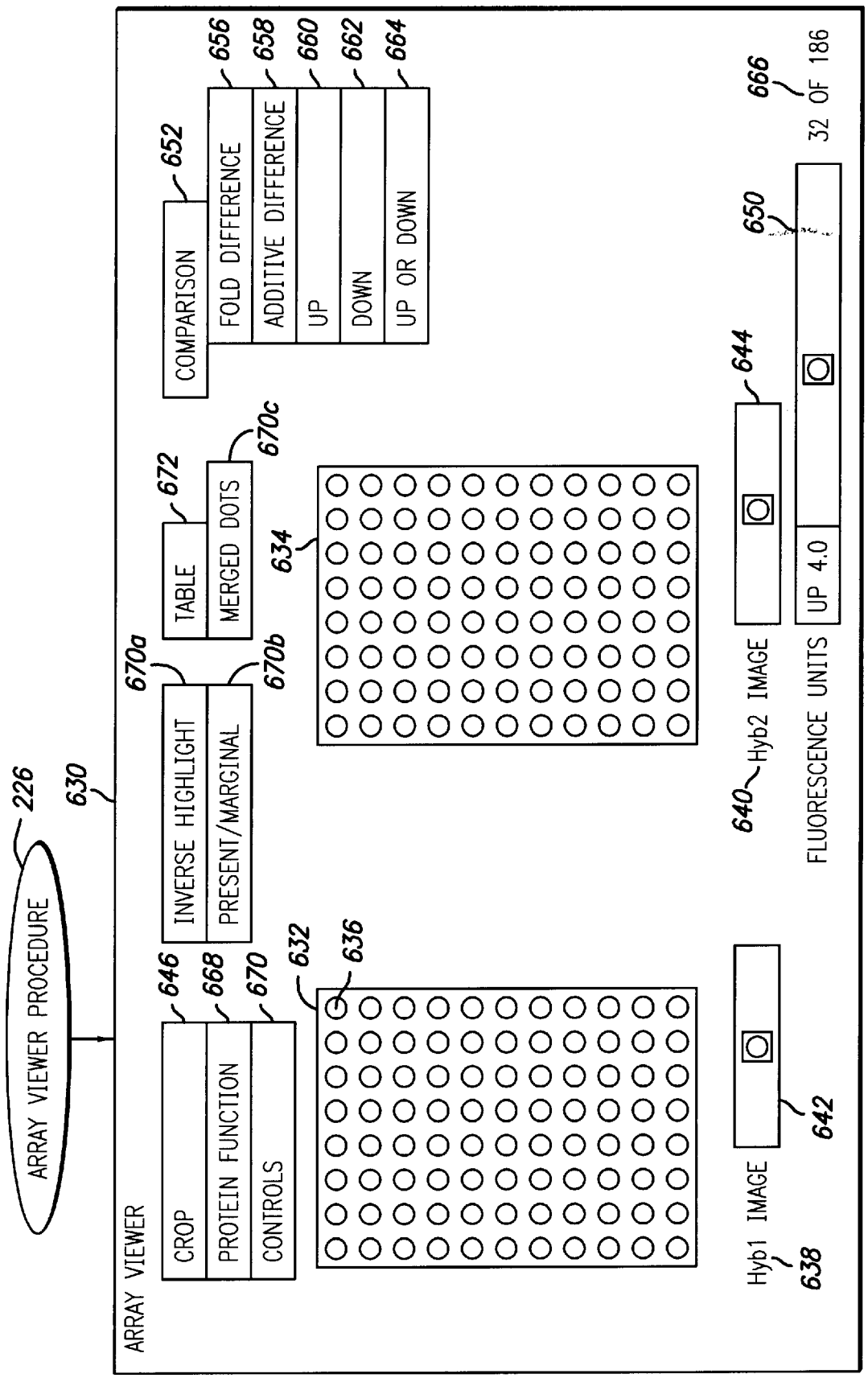
FIG. 11 depicts an exemplary sample array viewer window displaying two pseudoarrays on the graphical user interface.

Step 538 displays the pseudoarrays in one of the viewing tools (FIG. 11).

Another filter 540 allows a user to select specified elements of the dataset. The filter 540 includes a set of filtering tools, such as highlighting (selecting) and cropping.

In step 542, the user selects one of the filtering functions or tools of the filter. The user can filter by abundance, abundance fold difference, abundance absolute difference, transcript absence, controls or protein function. However, the invention is not meant to be limited to the previous filtering functions, in an alternate embodiment, other filtering functions are used.

Step 543 allows the user to choose one of the viewing tools to display the pseudoarrays. Viewing tools provide different display formats for the data. For example, an array viewer, table and multi-scatter, scatter viewers are provided. A merged dots view is available via the array viewer.

In addition, the system allows a user to import, display and compare data that is not stored in the expression database but is from an external dataset stored in a flat file (544). Step 546 executes an import external dataset procedure 208 (FIG. 4B) that reads that flat file and populates the JAVA objects for a pseudoarray with data from that flat file.

Figure 10A:
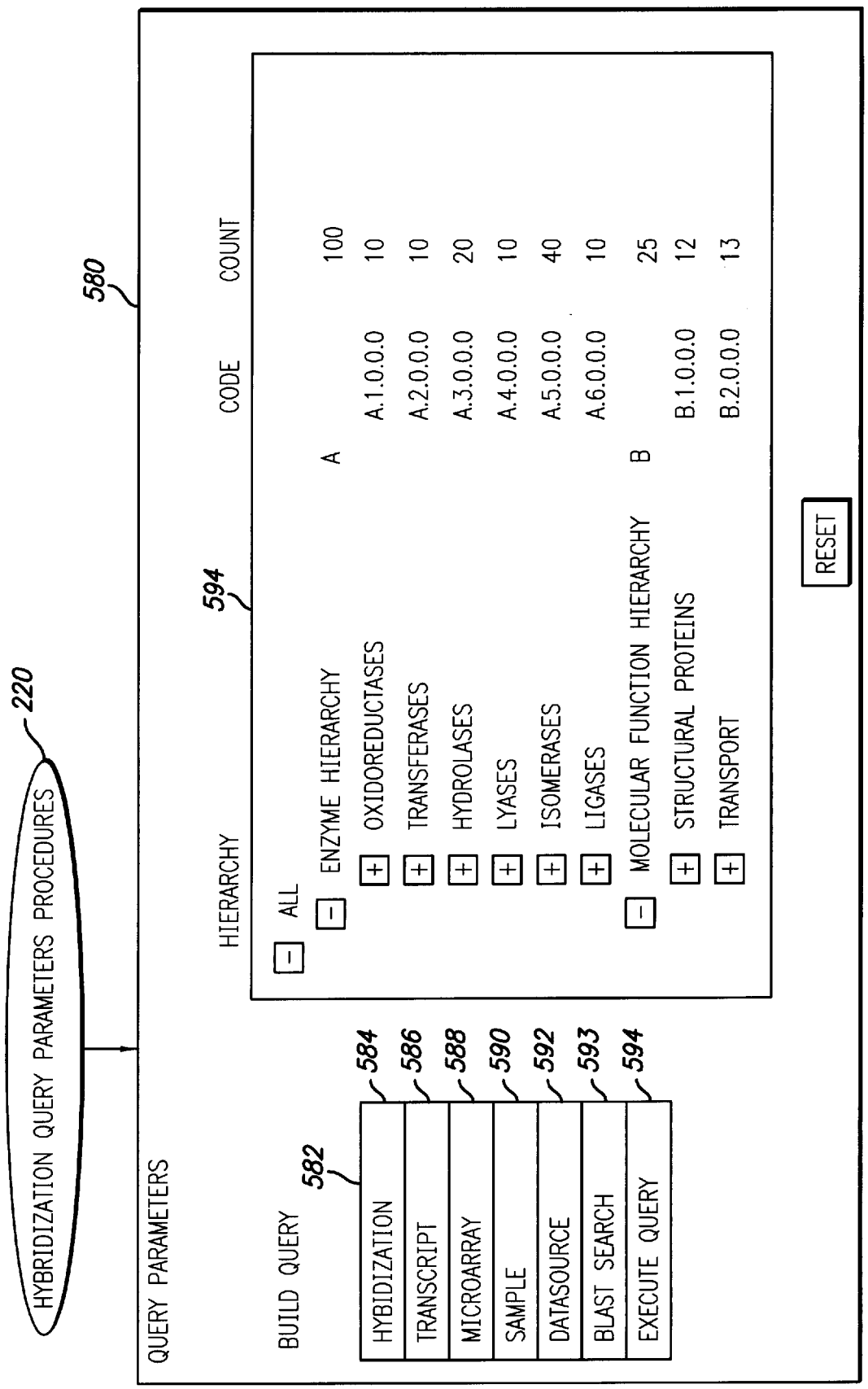
FIG. 10A is an exemplary hybridization query parameters window of the graphical user interface.

In FIG. 10A, a hybridization query parameters procedure 220 generates a query parameters window 580. A set of buttons 582 allows a user to select datasets using different parameters. The major query categories are hybridization 584, transcript 586, microarray 588, sample 590 and data source 592. The user can select any combination of query criteria by selecting data across these categories.

In response to the execute query button 593a, a generate list procedure 222 generates a dataset selection list 594. For example, in FIG. 10A, the transcript button 586 is selected and a hierarchical list is generated and displayed. The user selects one of the rows on the list by clicking on that row using a mouse.

Figure 10B:
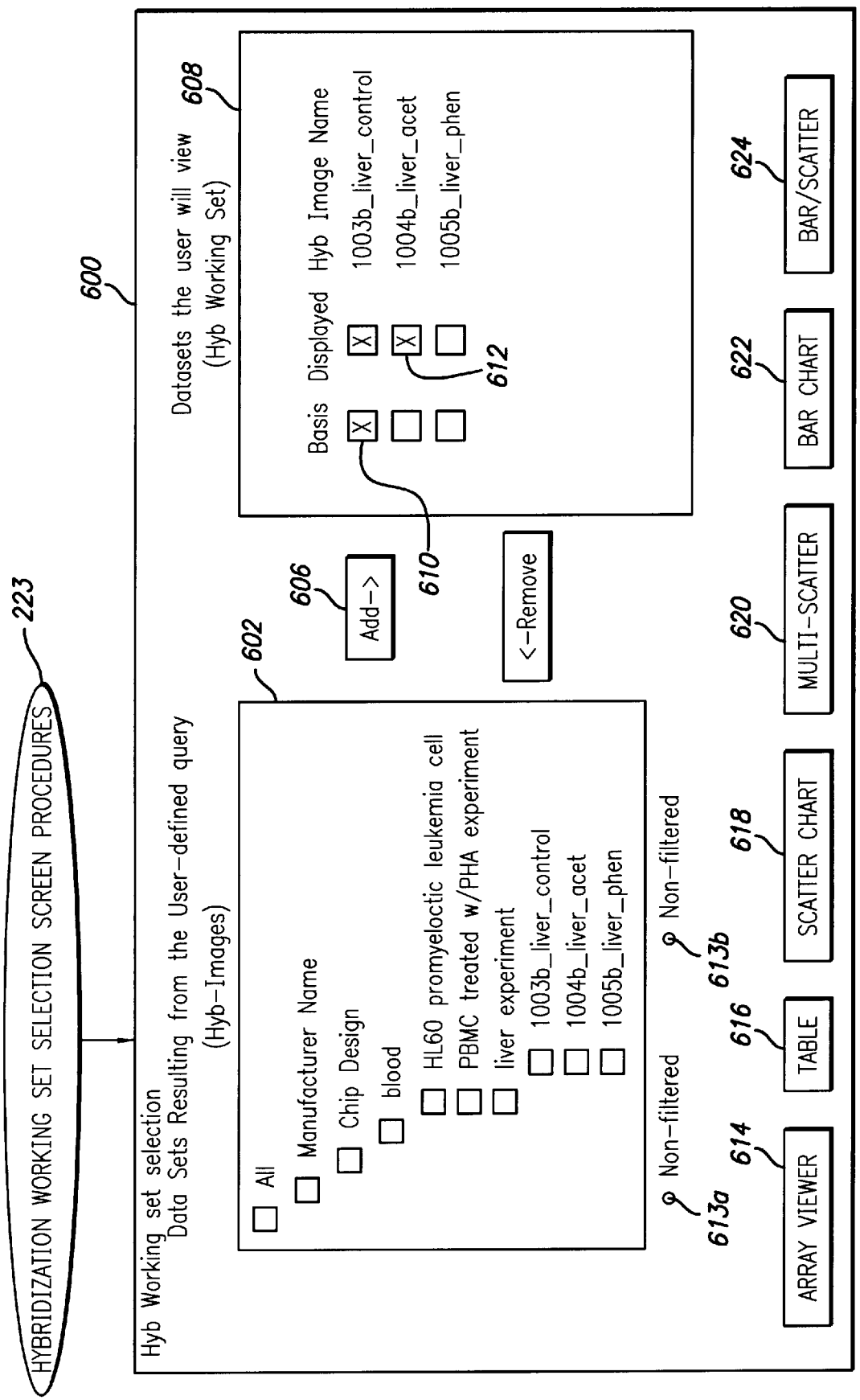
FIG. 10B is an exemplary hybridization working set selection window of the graphical user interface.

FIG. 10B depicts a hybridization working set selection screen window of the graphical user interface. In response to the selection on the hybridization query parameters window, a hybridization working set selection screen window procedure 223 generates the hybridization working set selection screen window 600. The hybridization working set selection screen procedure 223 includes the dataset selection procedure 224 (FIG. 4B), described above, and a selection screen builder procedure 225 (FIG. 4B). The dataset selection procedure 224 generates the list of hybridization abundance datasets 602 that are stored in the expression database. The selection screen builder procedure 225 generates the Hyb working set selection window 608 that lists the datasets that the user will view (Hyb Working Set).

To construct the Hyb working set, the user selects one or more abundance datasets from the list 602 by highlighting, then presses the add button 606 which initiates an add procedure 225a (FIG. 4B) that adds all information about all elements in the selected datasets to the hyb working set 608.

Within the hyb working set list 608, the user selects check boxes 610 to select the basis or base dataset for comparisons. Check boxes 612 are used to further select or deselect which datasets will be displayed in the viewers. After their selection is complete, the user can select on any one of the buttons below to display the selected abundance datasets in various formats. The buttons include an array viewer 614, table 616, scatter chart 618, multi-scatter 620, bar chart 622 and bar/scatter 624.

Radio buttons called "non-filtered" 613A and "filtered" 613B allow the user to enable or disable filter 533 of FIG. 9.

FIG. 11 depicts an exemplary sample array viewer window displaying two pseudoarrays on the graphical user interface. In response to pressing the array viewer button 622 (FIG. 10B), an array viewer procedure 226 generates the array viewer window 630. The array viewer window 630 displays abundance datasets from each selected dataset as a pseudoarray 632 and 634. The selected datasets can be from microarrays that use different technologies, such as absolute and competitive hybridization. The basis or base dataset is the leftmost dataset 632.

The pseudoarrays display a representation of the abundance values for the elements 636 of the pseudoarrays in the circles. The shape displayed is dependent on the display shape attribute stored in the Technology table in the database, such as squares. The circles are displayed on a black background. A color spectrum is used to indicate a range of abundance. The interior of the circles are color coded representations of the associated abundance value for that element. At one end of the scale, blue corresponds to the lower abundance values, while at the other end of the scale, red corresponds to the highest abundance values. The position of each element in the displayed pseudoarray does not necessarily reflect that element's position in the physical layout on the microarray. Alternately the elements can be displayed in the same row and column position as found on the physical microarray.

Figure 12:
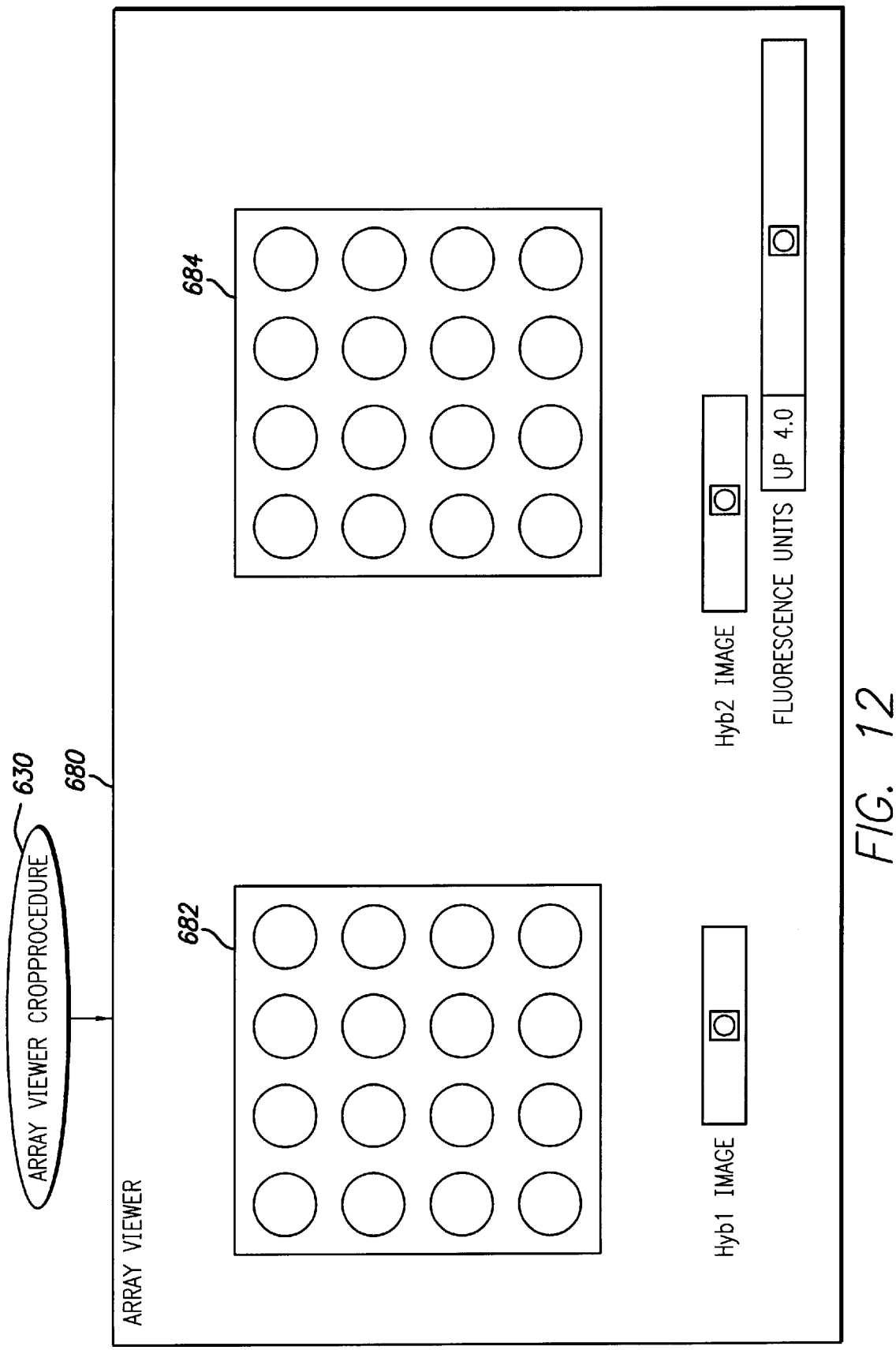
FIG. 12 depicts an exemplary cropped table view of a selected set of elements of the pseudoarrays of FIG. 11 on the graphical user interface.

The name of the hyb-image dataset 638, 640 and a rainbow slider 642, 644 is displayed beneath each displayed pseudoarray 632, 634. The rainbow slider 642, 644 displays the color spectrum from blue to red as described above. The colors on the slider correspond to the colors displayed in the pseudoarray elements for the abundance values. The rainbow slider is used to select sets of elements from each pseudoarray. The slider's position sets a first threshold abundance value. Those elements having abundance values exceeding the first threshold abundance value are outlined in white to indicate that those elements are selected or highlighted. When the rainbow slider under a pseudoarray changes the first threshold abundance value, all corresponding elements of all displayed pseudoarrays are outlined with respect to the new threshold value. Once elements are selected, a crop button 646 is pressed which eliminates those array elements that have not been highlighted. The result is a new pair of pseudoarrays that include the elements highlighted prior to the crop (FIG. 12).

The array viewer window 630 also has a multi-function fold/difference slider 650 which works with comparison menu button 652 to select various modes. Pressing the comparison button 652 causes a menu 654 to be displayed. The menu selections are fold difference 656, additive difference 658, up 660, down 662 and up-or-down 664. Fold Difference 656 puts the multi-function slider into a mode where fold differences are compared between the basis or base dataset and the other hybridization images. For each element, a fold difference is the difference between the abundance value of the element being compared from the abundance value of the base element divided by the basis element abundance. In other words, the following equation represents the fold difference:

fold difference=comparison element abundance/base element abundance

For example, if the comparison element abundance equals 150 and the base element abundance equals 50, then the fold difference equals 3. In other words, the fold difference is up three-fold from the base. In another example, if the comparison element abundance equals 20 and the base element abundance equals 100, then the fold difference equals 0.2, and the fold difference is down five-fold from the base.

Optionally, the user can set a detection limit and all negative values are set to that detection limit when calculating the fold difference. The detection limit is a positive real number.

Additive difference 658 puts the multi-function slider into a mode where the absolute difference in the abundance between the base and the other datasets is compared. The additive or absolute difference is determined using the following formula: absolute difference=comparison element abundance−base element abundance For both the fold difference and additive difference, the Up menu option 660 puts the multi-function slider into a mode to identify up regulation. Down puts the multi-function slider into a mode to identify down regulation. Up or down puts the multi-function slider into a mode to identify both up and down regulation. In other words, the slider identifies a range such as those values at least up 4 fold or down 4 fold. In an alternate embodiment, the slider identifies thoses values within a range.

Like the rainbow slider, the fold/difference slider 650 highlights selected elements with a white outline.

The number of selected elements 666 is also displayed such as "32 of 186." This indicates that of the 186 elements currently displayed, 32 of them are highlighted based on the use of the slider's position. The viewer tools have a highlight by protein function menu option 668 that allows a user to select elements by their associated protein function.

In addition, a highlight controls menu option 670 allows a user to highlight or select the elements designated as controls. An inverse highlight option 670A is provided to deselect those elements currently highlighted and highlight those elements not currently highlighted. A present/marginal menu option 670B allows a user to highlight those elements designated as being present or marginally present. A presence indicator field in the SummaryArrayElement table of the database designates P for present, M for marginal or A for absent.

A crop menu option 646 eliminates from the current view all elements not currently highlighted or selected.

FIG. 12 depicts an exemplary cropped view of a selected set of elements of the pseudoarrays of FIG. 11 on the graphical user interface. For simplicity, not all buttons and menu items of the array viewer of FIG. 11 are shown. In FIG. 11, after elements are highlighted and the crop button is pressed, a crop procedure 228 eliminates from the current view (the elements shown in FIG. 11) all elements not currently highlighted or selected. In other words, only the highlighted elements remain on the display.

This highlighting and cropping can be iteratively repeated to further narrow down the elements of interest.

The functions described above are available in all viewing tools.

FIGS. 13A and 13B depict two-types of exemplary drill-down windows for displaying detailed information of an element of interest. The drill-down window is an HTTP page. A drill-down window procedure 230 is generated in response to the mouse. As shown in FIG. 13A, if the right mouse button is clicked on an element of interest additional transcript information describing the element is displayed in drill-down window 694, 696 such as the abundance value, summarization value, normalization method and summarization method. As shown in FIG. 13B, if the left mouse button is clicked on an element of interest additional hybridization information describing the element is displayed in the drill-down window 690, 692 such as clone ID, Hit ID and Hit Description.

Figure 14:
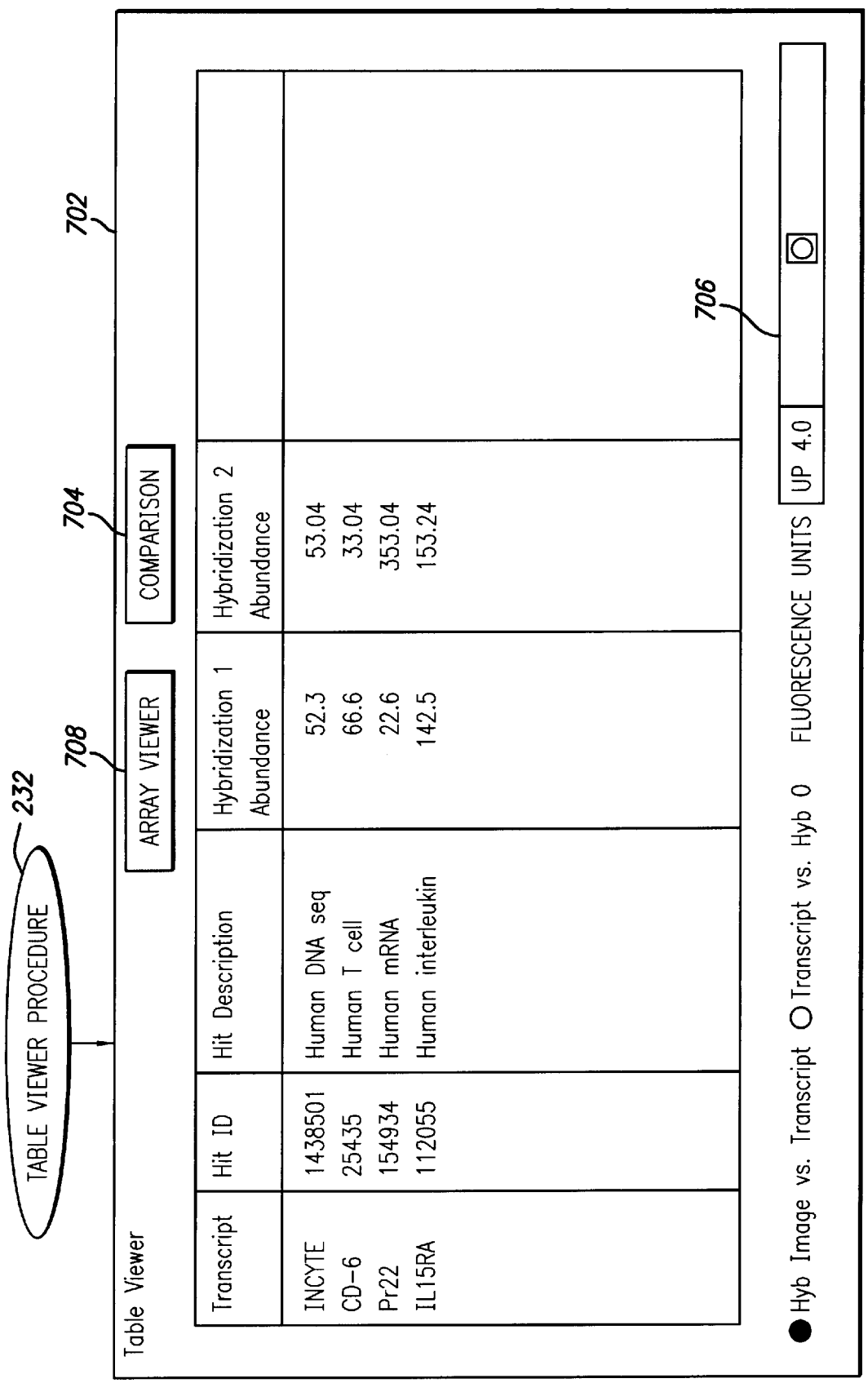
FIG. 14 depicts an exemplary table viewer window of the graphical user interface.

FIG. 14 depicts an exemplary table viewer window 702 of the graphical user interface. When the table menu option 672 on the Array Viewer window 630 of FIG. 11 is selected or when the table button 616 (FIG. 10B) is selected, a table viewer procedure 232 generates a table window 702 displaying the elements or selected elements by transcript, HitID, Hit Description followed by the abundance values for each hybridization. An array view button displays the data as pseudoarrays.

Highlighting in the table viewer, is done by using green and red highlighting of the abundance values. Green indicates up regulation and red indicates down regulation.

Figure 15:
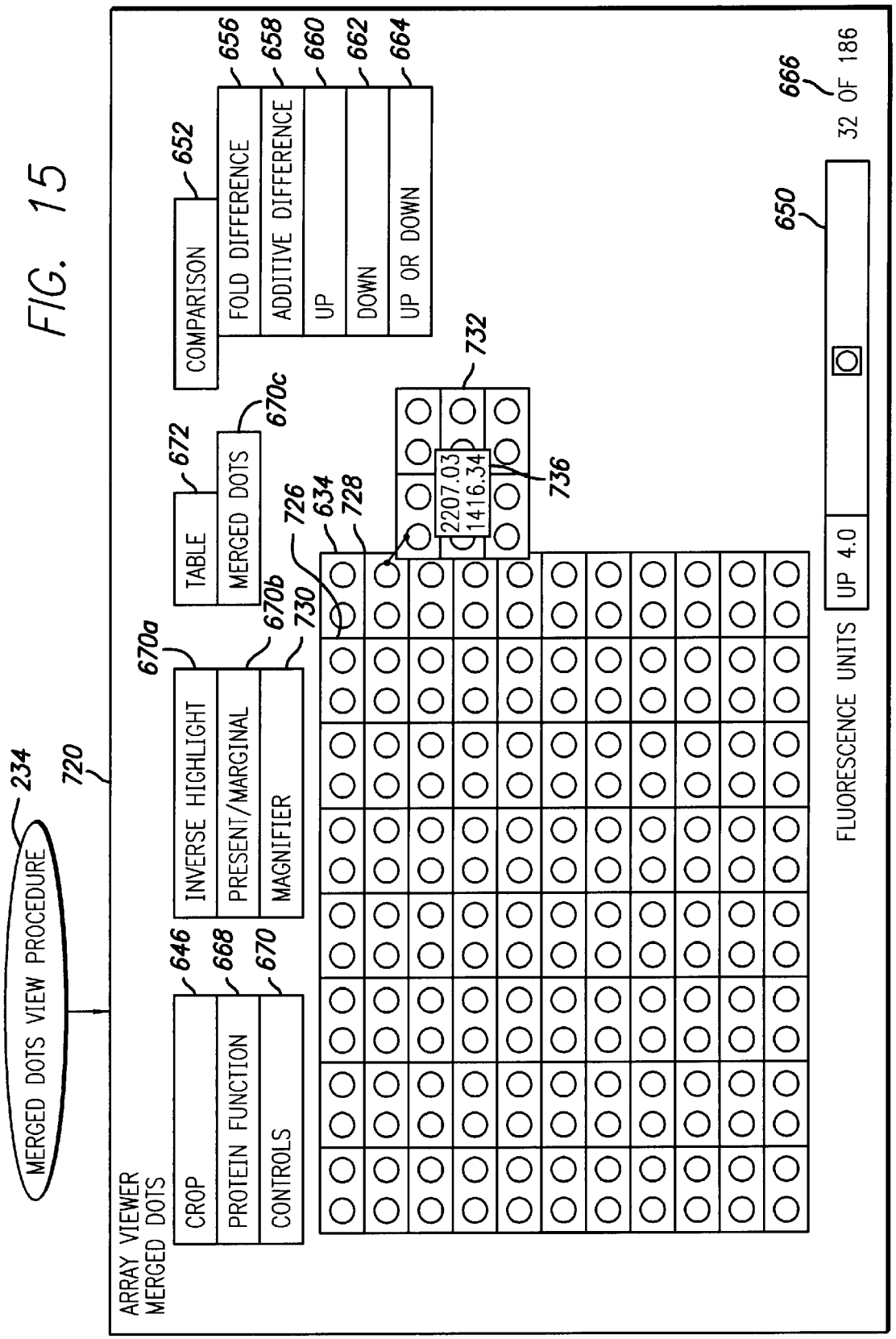
FIG. 15 depicts an exemplary merged dots view of the pseudoarrays of FIG. 11.

FIG. 15 depicts an exemplary merged dots view 720 of the graphical user interface. When the merged dots menu option 720c on the array viewer window 630 (FIG. 11) is selected, a merged dots view procedure 234 generates the merged dots view window 720. In this view, the abundance values for a specific gene across all datasets currently displayed are merged and displayed in groups 724. Lines 726 and 728 define the groups of merged dots. Each element in each group of merged dots has the same summary array element identifier (SummaryArrayElementID). A magnifier menu option 730 causes the popup window 732 to be displayed. The popup window displays a magnified view 732 of the elements in the group 734 under the cursor with their abundance values 736.

The term expression data includes not only transcripts and genes, but also refers to proteins and cell membranes. Alternately, expression data includes any material from which a level of expression can be obtained.

TABLE 1

| | Selected Field Definitions |
|---|---|
| HybID | - identifies a particular hybridization |
| Image ID | - identifies a particular image or scan (the raw expression values) of a hybridization. Many Image IDs can be associated with a single HybID. |
| PMDDataSource | - identifies the source of the loaded data. |
| SummaryElementID | - a unique identifier for each element's location on a microarray. |
| IntSummMethodID | - identifies a summarization method |
| AbunCalcMethodID | - identifies a normalization method |
| ArrayDesignID | - unique identifier for each microarray design |
| Technology type | - identifies the technology type of the microarray |
| ArrayPMDDataSource | - is an identifier for the source of the data for a microarray design, and is used to identify and associate a different data source for the microarray design used in a hybridization from the data source of the hybridization. |
| TranscriptAbundance | - the generated abundance intensity value |
| PresenceIndicator | - is A for absent, M for marginal and P for present |
| AbunCalcError | - an error value for the abundance |
| ArrayExperimentID | - unique identifier for an array experiment |
| PrepSampleID | - identifies a particular Prepared Sample |
| CommonGene | - indicates whether the gene is found commonly in the genome |
| ControlID | - unique identifier for each control |
| ControlSampleYN | - identifies whether the Sample is a control |
| NumArrayElements | - the number of elements or sites on the microarray |

TABLE 1-continued

| | Selected Field Definitions |
|---|---|
| SummaryRow | - designates the physical row for the element on the microarray |
| SummaryColumn | - designates the physical column for the element on the microarray |

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A method for storing normalized expression datasets from raw expression datasets, comprising:

storing one or more raw expression datasets derived from at least one microarray, wherein the at least one microarray includes nucleic acid probe sequences, wherein each raw expression dataset comprises a plurality of expression intensities of the nucleic acid probe sequences on the at least one microarray;

executing at least one normalization procedure that processes the raw expression datasets in accordance with the microarray design information associated with each raw expression dataset;

generating one or more normalized datasets from the raw expression datasets using one or more normalization procedures;

storing the normalized datasets based on the raw expression datasets and the procedures; and storing procedure identifiers representing the one or more procedures that were used to generate the normalized datasets from the raw expression datasets;

whereby one or more normalized datasets corresponding to a single raw expression dataset are stored.

2. The method of claim 1 further comprising:

selecting one of the normalized datasets as a base expression dataset;

selecting another of the normalized datasets as a comparison dataset; and generating a set of expression ratio values representing ratios of the expression intensities in the selected and base expression datasets.

3. The method of claim 1 wherein generating one or more normalized datasets comprises:

generating normalized data from a first raw expression dataset using a first normalization procedure, generating normalized data from the first raw expression dataset using a second normalization procedure;

wherein storing one or more normalized datasets includes:

storing a first normalized dataset based on the first raw expression dataset and the first normalization procedure;

storing a second normalized dataset based on the first raw expression dataset and the second normalization procedure; and wherein storing normalization procedure identifiers stores normalization procedure identifiers representing the first and second normalization procedures that were used to generate the first and second normalized datasets from the first raw expression dataset;

whereby two distinct normalized datasets corresponding to a single expression dataset are stored.

4. The method of claim 3 further comprising:

storing the first and second normalization procedures; and generating new normalized data from the first one of the raw expression datasets using a new normalization procedure;

storing a new normalized dataset based on the new normalized data and the new normalization procedure; and storing a new normalization procedure identifier representing the new normalization procedure; and storing the new normalization procedure.

5. The method of claim 3 wherein the first and second normalization procedures include first and second summarization methods, respectively, and a first normalization determination method, and further comprising:

storing the first and second summarization methods;

storing the first normalization determination method;

generating new summarization data from the first one of the stored raw expression datasets using a new summarization method;

storing the new summarization dataset based on the new summarization data and the new summarization method;

storing a summarization method identifier for the new summarization method;

storing the new summarization method;

generating new normalized data from the new summarization dataset using the first normalization determination method; and storing a new normalized dataset based on the new normalized data and first normalization determination method.

6. The method of claim 3 wherein the first and second procedures include first and second normalization determination methods, respectively, and further comprising:

storing a first summarization dataset based on the first one of the historical raw expression datasets and the first normalization procedure;

storing the first and second normalization determination methods;

generating new normalized data from the first summarization dataset using a new normalization determination method;

storing a new normalized dataset based on the new normalized data and new normalization determination method;

storing a normalization determination method identifier for the new normalization determination method; and storing the new normalization determination method.

7. The method of claim 1, further comprising storing the one or more procedures.

8. A biomolecular expression information processing system, comprising:

one or more tables for storing:

normalized datasets of expression intensities from nucleic acid probe sequences;

hybridization data that identifies, for each of at least a subset of the normalized datasets, a hybridization from which the normalized dataset was generated, the hybridization comprising a sample and microarray to which the sample was applied;

information identifying, for each hybridization, a microarray technology type;

microarray design information, for each microarray technology type, including technology data specifying global characteristics of each microarray instance of the microarray technology type;

array element data specifying characteristics of array elements of nucleic acid probe sequences in each microarray instance of the microarray technology type;

procedures, executed by the system, that process the normalized datasets in accordance with the microarray design information associated with each such normalized dataset;

wherein the system is capable of storing technology data for multiple distinct microarray technology types and is capable of storing array element data for multiple microarray designs of a single technology type.

9. The biomolecular expression information processing system of claim 8 wherein one microarray technology type generates a first raw expression dataset from a single hybridization, wherein the first raw expression dataset comprises a plurality of expression intensities of nucleic acid probe sequences.

10. The biomolecular expression information processing system of claim 8 wherein one microarray technology generates at least two raw expression datasets from a single hybridization, wherein the at least two raw expression datasets each comprise a plurality of expression intensities of nucleic acid probe sequences.

11. The biomolecular expression information processing system of claim 8 wherein one microarray technology type generates a first raw expression dataset for a single hybridization, and another microarray technology type generates at least two raw expression datasets from a single hybridization, wherein the first dataset and the at least two datasets each comprise a plurality of expression intensities of nucleic acid probe sequences.

12. The biomolecular expression information processing system of claim 7 further comprising:

a dataset comparison procedure that selects a first normalized dataset as a base expression dataset;

selects a second normalized dataset as a comparison dataset; and generates a set of expression ratio values representing ratios of expression intensities in the comparison and base expression datasets.

13. A method of processing biomolecular expression data, comprising:

selecting a set of expression datasets, wherein each expression dataset data comprises a plurality nucleic acid probe sequence elements;

selecting a subset of the elements in each of the selected expression datasets in accordance with specified selection criteria;

storing in one or more pseudoarrays the selected subset of elements for selected expression datasets; and using the one or more pseudoarrays, comparing corresponding elements of the different selected expression datasets to identify expression differences between the selected expression datasets.

14. The method of claim 13 wherein at least two of the selected expression datasets are associated with different microarray technologies.

15. The method of claim 13 wherein at least one expression dataset is from a microarray.

16. The method of claim 13 wherein at least one expression dataset is from an expression database.

17. The method of claim 13 wherein said step of selecting expression datasets includes the step of selecting a protein function, displaying identification information for expression datasets with elements having the selected protein function, selecting at least one expression dataset using the displayed identification information.

18. The method of claim 13 wherein at least a subset of the elements has an intensity, and said step of selecting a subset of the elements selects those elements having an intensity exceeding a predetermined threshold.

19. The method of claim 13 wherein at least a subset of the elements has an intensity, and said step of selecting a subset of the elements selects those elements having an intensity outside a predetermined range.

20. The method of claim 13 wherein at least a subset of the elements has an intensity, and said step of selecting a subset of the elements selects those elements having an intensity within a predetermined range.

21. The method of claim 13 wherein at least a subset of the elements has a hit description, and said step of selecting a subset of the elements selects those elements having a particular hit description.

22. The method of claim 13 wherein at least a subset of the elements has a transcript identifier, and said step of selecting a subset of the elements selects those elements having a particular transcript identifier.

23. The method of claim 13 wherein the pseudoarrays are compared by displaying the set of selected elements of each pseudoarray wherein each element is displayed as a colored spot with a color-coded intensity.

24. The method of claim 13 wherein the pseudoarrays are compared by displaying the set of identified elements in a table showing a numerical value for the intensity.

25. The method of claim 13 wherein selected expression datasets comprise a comparison expression dataset and a base expression dataset, and a set of expression ratio values are generated representing ratios of expression intensities in the comparison and base expression datasets.

26. The method of claim 13 wherein selected expression datasets comprise a comparison expression dataset and a base expression dataset, and a set of absolute expression values are generated representing a difference of expression intensities between the comparison and base expression datasets.

27. A computer-readable medium for storing instructions for a computer to store normalized expression datasets from raw expression datasets, the instructions comprising:

generating at least one normalized dataset from at least one raw expression dataset using at least one normalization, wherein the raw expression dataset comprises at least one expression intensity of nucleic acid probe sequences from at least one microarray; and storing the at least one normalized dataset based on the at least one raw expression dataset and the at least one procedure.

28. The computer-readable medium of claim 27, the instructions further comprising storing procedure identifiers representing the at least one procedure.

29. The computer-readable medium of claim 27, the instructions further comprising storing the at least one raw expression dataset.

30. The computer-readable medium of claim 27, wherein the at least one normalized dataset includes a first normalized dataset and a second normalized dataset, the instructions further comprising:

selecting the first normalized dataset as a base expression dataset;

selecting the second normalized dataset as a comparison dataset; and generating a set of expression ratio values representing ratios of the expression intensities in the comparison and base expression datasets.

31. The computer-readable medium of claim 27, the instructions further comprising storing the at least one procedure.

32. The computer-readable medium of claim 27, the instructions further comprising summarizing the at least one expression intensity using a summarization method.

33. The computer-readable medium of claim 32, the instructions further comprising storing the summarization method.

34. The computer-readable medium of claim 32, the instructions further comprising storing summarization method identifiers representing the summarization method.

35. A computer-readable medium for storing instructions for a computer to process biomolecular expression data, the instructions comprising:

selecting a set of expression datasets, each expression dataset having a plurality of nucleic acid probe sequence elements;

selecting a subset of the elements in each of the selected expression datasets in accordance with specified selection criteria;

storing in one or more pseudoarrays the selected subset of elements for selected expression datasets; and using the one or more pseudoarrays, comparing corresponding elements of the different selected expression datasets to identify expression differences between the selected expression datasets.

36. The computer-readable medium of claim 35 wherein at least two of the selected expression datasets are associated with different microarray technologies.

37. The computer-readable medium of claim 35 wherein at least one expression dataset is from a microarray.

38. The computer-readable medium of claim 35 wherein at least one expression dataset is from an expression database.

39. The computer-readable medium of claim 35 wherein selecting expression datasets includes selecting a protein function, displaying identification information for expression datasets with elements having the selected protein function, selecting at least one expression dataset using the displayed identification information.

40. The computer-readable medium of claim 35 wherein at least a subset of the elements has an intensity, and selecting a subset of the elements selects those elements having an intensity exceeding a predetermined threshold.

41. The computer-readable medium of claim 35 wherein at least a subset of the elements has an intensity, and selecting a subset of the elements selects those elements having an intensity outside a predetermined range.

42. The computer-readable medium of claim 35 wherein at least a subset of the elements has an intensity, and selecting a subset of the elements selects those elements having an intensity within a predetermined range.

43. The computer-readable medium of claim 35 wherein at least a subset of the elements has a hit description, and selecting a subset of the elements selects those elements having a particular hit description.

44. The computer-readable medium of claim 35 wherein at least a subset of the elements has a transcript identifier, and selecting a subset of the elements selects those elements having a particular transcript identifier.

45. The computer-readable medium of claim 35 wherein the pseudoarrays are compared by displaying the set of selected elements of each pseudoarray wherein each element is displayed as a colored spot with a color-coded intensity.

46. The computer-readable medium of claim 35 wherein the pseudoarrays are compared by displaying the set of identified elements in a table showing a numerical value for the intensity.

47. The computer-readable medium of claim 35 wherein selected expression datasets comprise a comparison expression dataset and a base expression dataset, and a set of expression ratio values are generated representing ratios of expression intensities in the comparison and base expression datasets.

48. The computer-readable medium of claim 35 wherein selected expression datasets comprise a comparison expression dataset and a base expression dataset, and a set of absolute expression values are generated representing a difference of expression intensities between the comparison and base expression datasets.

49. A system to store normalized expression datasets from raw expression datasets, comprising:

means for generating at least one normalized dataset from at least one raw expression dataset using at least one normalization procedure, wherein the raw expression dataset comprises at least one expression intensity of nucleic acid probe sequences from at least one microarray; and means for storing the at least one normalized dataset based on the at least one raw expression dataset and the at least one procedure.

50. A system for processing biomolecular expression data, comprising:

means for selecting a set of expression datasets, each expression dataset having a plurality of nucleic acid probe sequence elements;

means for selecting a subset of the elements in each of the selected expression datasets in accordance with specified selection criteria;

means for storing in one or more pseudoarrays the selected subset of elements for selected expression datasets; and means for using the one or more pseudoarrays, comparing corresponding elements of the different selected expression datasets to identify expression differences between the selected expression datasets.

* * * * *

UNITED STATES PATENT AND TRADEMARK OFFICE
CERTIFICATE OF CORRECTION

PATENT NO. : 6,408,308 B1
DATED : June 18, 2002
INVENTOR(S) : Maslyn et al.

It is certified that error appears in the above-identified patent and that said Letters Patent is hereby corrected as shown below:

Column 18,
Line 41, change "system of claim 7 further comprising" to -- system of claim 8 further comprising --

Signed and Sealed this

Eighteenth Day of March, 2003

JAMES E. ROGAN
*Director of the United States Patent and Trademark Office*